United States Patent
Freedman et al.

(10) Patent No.: US 9,459,330 B2
(45) Date of Patent: Oct. 4, 2016

(54) SYSTEM AND METHOD FOR OBTAINING NUCLEAR MAGNETIC RESONANCE MEASUREMENTS ON RESERVOIR FLUIDS FOR PREDICTION OF FLUID PROPERTIES

(71) Applicant: Schlumberger Technology Corporation, Sugar Land, TX (US)

(72) Inventors: Robert Freedman, Houston, TX (US); Vivek Anand, Houston, TX (US); Payam Tabrizi, Missouri, TX (US); Ricardo Y. Torres, Manvel, TX (US); Douglas W. Grant, Cedar Creek, TX (US); Daniel Catina, Cypress, TX (US); Krishnamurthy Ganesan, Sugar Land, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 843 days.

(21) Appl. No.: 13/827,549

(22) Filed: Mar. 14, 2013

(65) Prior Publication Data
US 2014/0253116 A1    Sep. 11, 2014

Related U.S. Application Data

(60) Provisional application No. 61/772,826, filed on Mar. 5, 2013.

(51) Int. Cl.
*G01R 33/30* (2006.01)
*G01N 24/08* (2006.01)
*G01V 3/32* (2006.01)

(52) U.S. Cl.
CPC .............. *G01R 33/30* (2013.01); *G01N 24/081* (2013.01); *G01R 33/305* (2013.01); *G01V 3/32* (2013.01)

(58) Field of Classification Search
CPC .. G01R 33/30; G01R 33/305; G01N 24/081; G01V 3/32
See application file for complete search history.

(56) References Cited

U.S. PATENT DOCUMENTS

| 4,710,713 A | 12/1987 | Strikman |
| 5,696,448 A | 12/1997 | Coates et al. |

(Continued)

FOREIGN PATENT DOCUMENTS

EP    932055 A2    7/1999

(Continued)

OTHER PUBLICATIONS

Anand, et al., "New Method for Predicting Properties of Live Oils from NMR", Petrophysics, vol. 53, 2012, pp. 256-271.

(Continued)

*Primary Examiner* — Dixomara Vargas
(74) *Attorney, Agent, or Firm* — John Vereb

(57) ABSTRACT

A nuclear magnetic resonance (NMR) measurement system for high pressure and temperature measurements on fluids is disclosed. The system has a sensor assembly that includes a sample holder having a body formed from a non-magnetic metal and defining an interior cavity for receiving a fluid sample, a frame member disposed in the interior cavity of the sample holder, an antenna coil disposed in the interior cavity about the frame member, an inlet that allows the fluid sample to enter the interior cavity, an outlet that allows for the fluid sample to be flushed from the interior cavity, and a magnet assembly having a central bore in which the sample holder is disposed. Adjacent to the sample holder are pulsed field gradient coils for performing diffusion measurements. The system further includes pulse sequencer circuitry that supplies signals to the antenna coil. When the interior cavity of the sample holder is filled with the fluid sample, the antenna coil and the frame member are at least partially submerged in the fluid sample, and the antenna coil obtains NMR measurements of the fluid sample in response to the signals. Related methods and apparatuses are also disclosed herein.

10 Claims, 24 Drawing Sheets

(56) References Cited

U.S. PATENT DOCUMENTS

| | | | | |
|---|---|---|---|---|
| 6,891,369 | B2* | 5/2005 | Hurlimann | G01N 24/081 324/303 |
| 7,053,611 | B2* | 5/2006 | Freedman | G01V 3/32 324/300 |
| 7,253,618 | B1 | 8/2007 | Freedman et al. | |
| 7,309,983 | B2 | 12/2007 | Freedman | |
| 7,683,613 | B2* | 3/2010 | Freedman | G01N 24/081 324/303 |
| 8,794,318 | B2* | 8/2014 | Harrigan | E21B 49/008 166/100 |
| 2002/0140425 | A1 | 10/2002 | Prammer et al. | |
| 2012/0049844 | A1 | 3/2012 | Leveridge et al. | |
| 2012/0065888 | A1 | 3/2012 | Wu et al. | |

OTHER PUBLICATIONS

Freedman, et al., "A Modern Method for Using Databases to Obtain Accurate Solutions to Complex Reservoir Characterization Problems", SPE Reservoir Evaluation and Engineering, vol. 15, 2012, pp. 453-461.

Freedman, et al., "A New NMR Method of Fluid Characterization in Reservoir Rocks: Experimental Confirmation and Simulation Results", SPE 63214, 2000 Society of Petroleum Engineers Annual Technical Conference and Exhibition, Dallas, Texas, 2000, pp. 1-15.

Freedman, et al., "Combining NMR and Density Logs for Petrophysical Analysis Gas-Bearing Formations", SPWLA Annual Logging Symposium, May 1998, 1998, 14 pages.

Freedman, et al., "Fluid Characterization using Nuclear Magnetic Resonance Logging", Petrophysics, vol. 45 (3), 2004, pp. 241-250.

Freedman, et al., "New Approach for Solving Inverse Problems Encountered in Well-Logging and Geophysical Applications", Petrophysics, vol. 47, No. 2, Apr. 2006, pp. 93-111.

Harris, "Temperature and Density Dependence of the Self-Diffusion Coefficient of n-Hexane from 223 to 333K and up to 400 MPa", Journal of the Chemical Society, Faraday Transactions 1: Physical Chemistry in Condensed Phases, vol. 78, 1982, pp. 2265-2274.

Hurlimann, et al., "Hydrocarbon Composition from NMR Diffusion and Relaxation Data", Petrophysics, vol. 50, 2009, pp. 116-129.

Krynicki, et al., "Pressure and Temperature Dependence of Self-Diffusion in Water", Faraday Discussion of the Chemical Society, vol. 66, 1978, pp. 199-208.

Lo, et al., "Correlations of NMR Relaxation Time with Viscosity, Diffusivity, and Gas/Oil Ratios of Methane/ Hydrocarbon Mixtures", SPE 63217, Society of Petroleum Engineers, presented at the SPE Annual Technical Conference and Exhibition, 2000, pp. 1-15.

Stejskal, et al., "Spin Diffusion Measurements: Spin Echoes in the Presence of a Time-Dependent Field Gradient", Journal of Chemical Physics, vol. 42, 1965, pp. 288-292.

Von Meerwall, et al., "Diffusion of Liquid n-alkanes, Free-vol. And Density Effects", Journal of Chemical Physics, vol. 108, 2004, pp. 4299-4304.

Winkler, et al., "The Limits of Fluid Property Correlations Used in NMR Well Logging: An Experimental Study of Reservoir Fluids at Reservoir Conditions", 45th SPWLA Annual Logging Symposium Transactions, 2004, pp. 1-13.

Zhang, et al., "Oil and Gas NMR Properties: The Light and Heavy Ends", 43rd Annual SPWLA Annual Logging Symposium Transactions: Society of Petrophysicists and Well Log Analysts, 2002, pp. 1-13.

Zielinski, et al., "Nuclear Magnetic Resonance Dispersion of Distributions as a Probe of Aggregation in Crude Oils", Energy & Fuels, vol. 25, 2011, pp. 5090-5099.

International Search Report and Written Opinion issued in PCT/US2014/020501 on Jun. 2, 2014, 29 pages.

* cited by examiner

EXAMPLE OIL 1
D-T2 MAPS
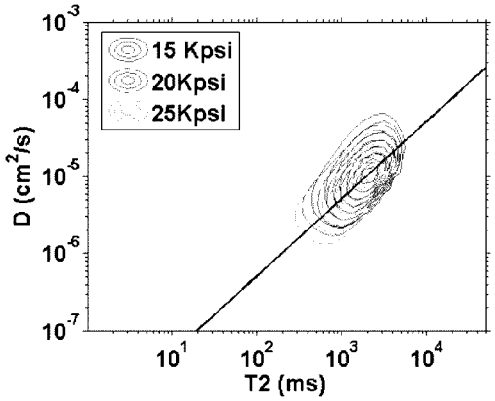
D-T2 MAP
Temp: 175C
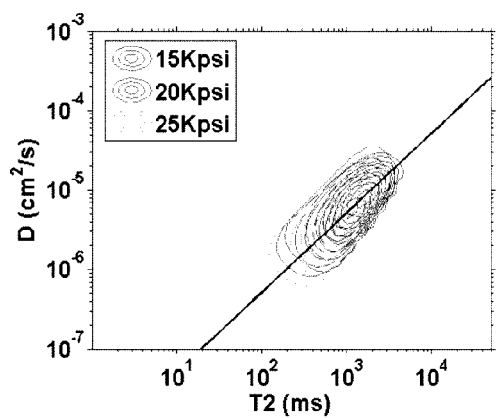
*FIG. 5A*
D-T2 MAP
Temp: 125C
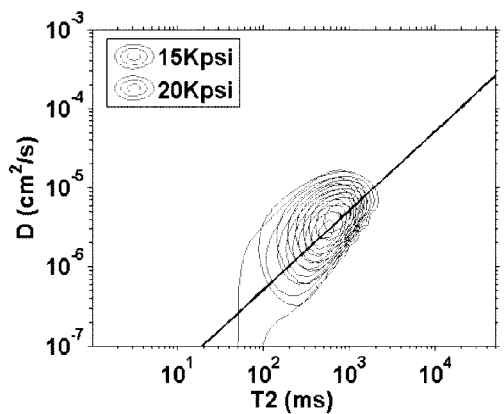
D-T2 MAP
Temp: 75C T1-T2 MAP
Temp: 175C T1-T2 MAP
Temp: 125C T1-T2 MAP
Temp: 75C

EXAMPLE OIL 2
D-T2 MAPS
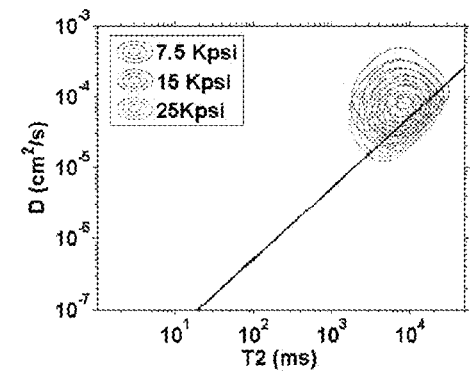
D-T2 MAP
Temp: 175C
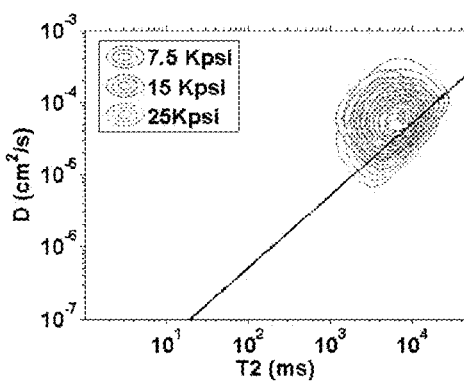
*FIG. 6A*
D-T2 MAP
Temp: 125C
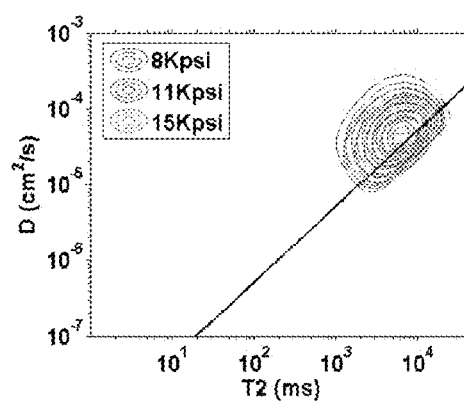
D-T2 MAP
Temp: 75C

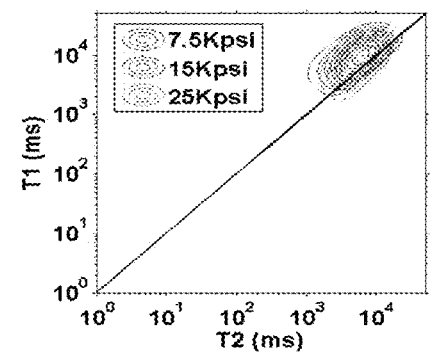
T1-T2 MAP
Temp: 175C
*FIG. 6B*
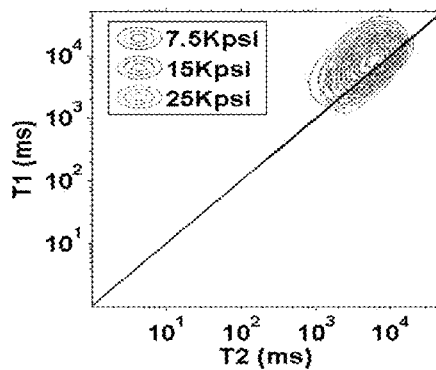
T1-T2 MAP
Temp: 125C
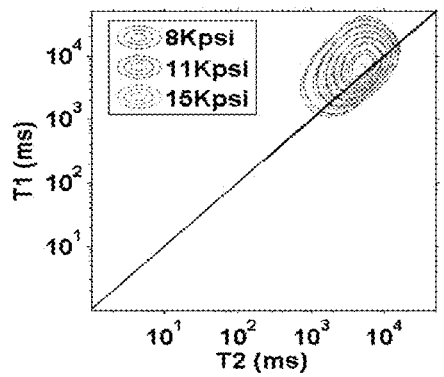
T1-T2 MAP
Temp: 75C D-T2 MAP
Temp: 175C D-T2 MAP
Temp: 125C D-T2 MAP
Temp: 75C

**EXAMPLE OIL 3
T1-T2 MAPS**
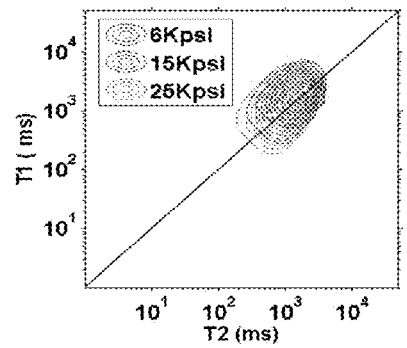
T1-T2 MAP
Temp: 175C
*FIG. 7B*
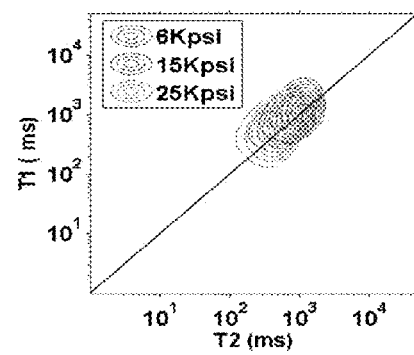
T1-T2 MAP
Temp: 125C
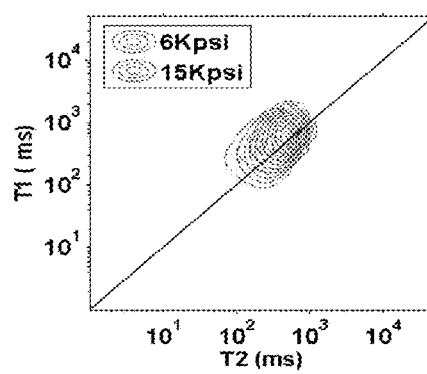
T1-T2 MAP
Temp: 75C

SYSTEM AND METHOD FOR OBTAINING NUCLEAR MAGNETIC RESONANCE MEASUREMENTS ON RESERVOIR FLUIDS FOR PREDICTION OF FLUID PROPERTIES

CROSS-REFERENCE TO RELATED APPLICATION

This application claims priority to and the benefit of a related U.S. Provisional Patent Application Ser. No. 61/772,826, filed Mar. 5, 2013, entitled "System And Method For Obtaining Nuclear Magnetic Resonance Measurements On Reservoir Fluids For Prediction of Fluid Properties," the disclosure of which is incorporated by reference herein in its entirely.

BACKGROUND

This section is intended to introduce the reader to various aspects of art that may be related to various aspects of the subject matter described and/or claimed below. This discussion is believed to be helpful in providing the reader with background information to facilitate a better understanding of the various aspects of the present disclosure. Accordingly, it should be understood that these statements are to be read in this light, not as admissions of prior art.

The present disclosure relates generally to techniques for using nuclear magnetic resonance (NMR) to acquire data indicative of the properties of hydrocarbons and, more specifically, to an NMR measurement system for acquiring data of the properties of live oils at temperatures and pressures reflective of realistic reservoir conditions.

Oil and gas exploration and production are very expensive operations. Any knowledge about the formations that can help reduce the unnecessary waste of resources in well drilling will be invaluable. Therefore, the oil and gas industry has developed various tools capable of determining and predicting earth formation properties. Among different types of tools, nuclear magnetic resonance (NMR) instruments have proven to be invaluable. NMR instruments can be used to determine formation properties, such as the fractional volume of pore space and the fractional volume of mobile fluid filling the pore space.

The introduction of pulsed nuclear magnetic resonance (NMR) logging tools in the early 1990's brought to the industry new capabilities for characterization of oil and gas bearing reservoirs. These tools employ diffusion encoded pulse sequences that can be used to separate oil, gas, and water signals based on contrasts in the molecular diffusion coefficients of the fluids (See, Freedman et al., "*A New Method of Fluid Characterization in Reservoir Rocks: Experimental Confirmation and Simulation Results*," SPE Paper 63214 (2000); see also Freedman et al., "*Fluid Characterization Using Nuclear Magnetic Resonance Logging*," Petrophysics, vol. 45, p. 241-250 (2004)). Thus, NMR diffusion-based fluid typing provided the industry with a tool for identifying oil and gas reservoirs. Additionally, NMR logging provided the density-magnetic resonance method for identifying and evaluating gas-bearing zones (See Freedman et al., "*Combining NMR and Density Logs for Petrophysical Analysis in Gas Bearing Formations*," SWPLA, 39th Annual Logging Symposium (1998)).

In general, NMR provides an excellent non-invasive technique for studying the microscopic molecular interactions in fluid systems and, therefore, it provides a means for predicting molecular and macroscopic petroleum fluid properties. The temperature and pressure dependence of molecular interactions governing the NMR response provides an understanding of the dynamical processes in such systems. Furthermore, NMR measurements of relaxation time and diffusion coefficients of fluids are related to macroscopic properties which are strongly temperature and pressure dependent. However, in spite of the successes in fluid typing and the prediction of near wellbore reservoir fluid volumes, the accurate prediction of reservoir fluid properties (e.g., viscosity, fluid density, molecular composition, saturates, aromatics, resins, and asphaltene (SARA) fractions, gas-oil ratio (GOR), etc.) using NMR-related techniques has made little progress.

It is believed that the lack of progress in this regard can be attributed to several factors. First, crude oils are complex and variable mixtures of organic and inorganic molecules containing different amounts and types of dissolved gas molecules. This complexity cannot be accurately described by the simple idealized models that are commonly used in the industry (See Freedman et al., "*A Modern Method for Using Databases to Obtain Accurate Solutions to Complex Reservoir Characterization Problems*," SPE Reservoir Evaluation and Engineering, vol. 15, pp. 453-461 (2012)). It became realized that accurate prediction of fluid properties from NMR required a model-independent approach to address the inherent complexity of crude oils. Second, there were no known extensive databases of NMR, PVT (pressure/volume/temperature), and physical properties data acquired on live oils at realistic reservoir conditions. Such databases are important for the development and validation of the accuracy of NMR-based predictive methods.

The problem of reservoir fluid complexity was at least partly addressed in Freedman et al., "*New Approach for Solving Inverse Problems Encountered in Well-Logging and Geophysical Applications*," Petrophysics, vol. 47, pp. 93-111 (2006), which describes a model-independent method for accurately solving inverse problems for complex systems. This method uses a general model-independent mapping function to approximate the unknown functional relationship between the NMR measurements and the fluid properties to be predicted. The mapping function can be uniquely determined from a database of NMR and fluid properties measurements and can be expressed in analytical form as a summation of Gaussian radial basis functions (RBF). In summary, this model-independent method addresses the notion that while crude oils are too complex to be accurately described by simple models, the physics are contained in the database and can be represented by a general non-linear mapping function. As described in the above-referenced Freedman 2006 publication, this mapping function methodology was tested on a small database of dead oils (oils without dissolved gases) and obtained encouraging results from the predictions of viscosity and molecular composition. Accordingly, the results showed that the foregoing method has the potential to predict accurate fluid properties of live oils from a database of NMR, PVT, and fluid properties measurements.

Additional studies and experimentation were performed using an NMR measurement system in a laboratory setting to assess the viability of the above-described mapping function methodology when applied to a database of live oils, as described in Anand et al., "*New Method for Predicting Properties of Live Oils from NMR*," Petrophysics, vol. 53, pp. 256-271 (2012). The NMR measurement system was installed by Schlumberger Technology Corporation and included a 2 MHz spectrometer (e.g., a commercial Resonance Instruments Maran spectrometer). The NMR measurement system also included a pressure cell for making NMR measurements on single phase live oils (e.g., based on a commercial pressure model by Temco, Inc.). This study provided encouraging results showing that important fluid properties, including molecular composition, viscosity, and SARA fractions could be predicted with reasonable accuracy from a relatively sparse database using this mapping function method. However, the installed commercial system described in Anand et al. 2012 had significant limitations and was not a viable system for the acquisition of an extensive database of NMR measurements at realistic conditions of temperature and pressure. For instance, the Anand et al. 2012 NMR measurement system was restricted to pressure and temperature limits of about 10 kpsi and 110 degrees C., both of which falls far short of the 25 kpsi and 175 degrees centigrade (C) representative of real conditions in some worldwide oil reservoirs. Another serious limitation of the Anand et al. 2012 system was its relatively low signal-to-noise ratio (SNR) (e.g., 15:1), which required very long measurement times (e.g., more than 12 hours for pulsed field gradient diffusion measurements) at each pressure and temperature.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

The present disclosure relates to a new and innovative high performance measurement system for performing low field nuclear magnetic resonance (NMR) relaxation time and diffusion measurements. This NMR measurement system is capable of enabling a study of reservoir fluids at the high temperatures and pressures encountered in many oil and gas reservoirs. In accordance with one aspect of this disclosure. One objective of such a study was to determine which reservoir fluid properties can be predicted from NMR measurements and the accuracy of any such predictions. Another objective of the study was to determine if combining NMR data with near-infrared optical absorption data improved the predictions.

As generally mentioned in the Background Section above, previous industry publications (e.g., Anand et al. 2012) on reservoir fluid studies using NMR have been based on measurements acquired using commercial NMR systems, which often lack the ability to acquire reliable NMR measurements at meaningful pressure and/or temperature limits, and also generally have inadequate signal-to-noise ratios. The temperature and pressure specifications and signal-to-noise ratio (SNR) of the NMR measurement system described in this disclosure represents a significant improvement in the technology compared to those of commercially available systems.

Embodiments of the high performance NMR measurement system include a compact sensor having an NMR magnet with a low static magnetic field gradient, an RF antenna, and a pair of pulse filed gradient (PFG) coils which may be used for NMR diffusion measurements. Using such a system, high quality NMR data on live reservoir fluids can be rapidly acquired at the high temperatures and pressures typically encountered in worldwide oil reservoirs. The SNR of the disclosed system is also significantly improved when compared to existing commercial systems, such as by more than a factor of ten. By way of example, embodiments of the disclosed NMR measurement system may have an SNR of between 100:1 and 250:1 or greater. Accordingly, data acquisition can be as much as one hundred times faster than previously possible. Moreover, the system is relatively easy to maintain and pressure compensation is not required to achieve high pressures.

In practice, the disclosed NMR measurement system was used to acquire a database of hundreds of NMR and optics measurements at different temperatures and pressures on a representative suite of oils typical of those sampled by fluid sampling tools. In addition, to the NMR and optics measurements, the database contains measured fluid properties including molecular compositions, SARA fractions, GOR, bubble point, viscosity, compressibility, formation volume factor, and density measurements for each oil. The NMR, optics, and fluid properties measurements were made at pressures up to 25 kpsi and at temperatures up to 175 C. This database may then be used to determine how accurately fluid properties (including molecular composition, SARA fractions, viscosity, GOR, density, and compressibility) can be predicted from the NMR measurements. The present disclosure thus provides a discussion of the NMR measurement system, sample preparation, the acquisition of measurements, and the accuracy of the predictions. Using this system, each of the aforementioned reservoir fluid properties can be accurately predicted from NMR measurements given the pressure and temperature of the reservoir fluid.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. Again, the brief summary presented above is intended only to familiarize the reader with certain aspects and contexts of embodiments of the present disclosure without limitation to the claimed subject matter.

BRIEF DESCRIPTION OF THE DRAWINGS

Various aspects of this disclosure may be better understood upon reading the following detailed description and upon reference to the drawings in which:

FIGS. 5A and 5B show D-$T_2$ maps and $T_1$-$T_2$ maps, respectively, for a first live oil sample obtained at various pressures and temperature using the sample holder of FIG. 2;

FIGS. 6A and 6B show D-$T_2$ maps and $T_1$-$T_2$ maps, respectively, for a second live oil sample obtained at various pressures and temperature using the sample holder of FIG. 2;

FIGS. 7A and 7B show D-$T_2$ maps and $T_1$-$T_2$ maps, respectively, for a third live oil sample obtained at various pressures and temperature using the sample holder of FIG. 2;

DETAILED DESCRIPTION

One or more specific embodiments are described below. These embodiments are only examples of the presently disclosed techniques. Additionally, in an effort to provide a concise description of these embodiments, all features of an actual implementation may not be described in the specification. It should be appreciated that in the development of any such implementation, as in any engineering or design project, numerous implementation-specific decisions are made to achieve the developers' specific goals, such as compliance with system-related and business-related constraints, which may vary from one implementation to another. Moreover, it should be appreciated that such development efforts might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. The embodiments discussed below are intended to be examples that are illustrative in nature and should not be construed to mean that the specific embodiments described herein are necessarily preferential in nature. Additionally, it should be understood that references to "one embodiment" or "an embodiment" within the present disclosure are not to be interpreted as excluding the existence of additional embodiments that also incorporate the recited features.

Section 1: Introduction

Figure 1A:
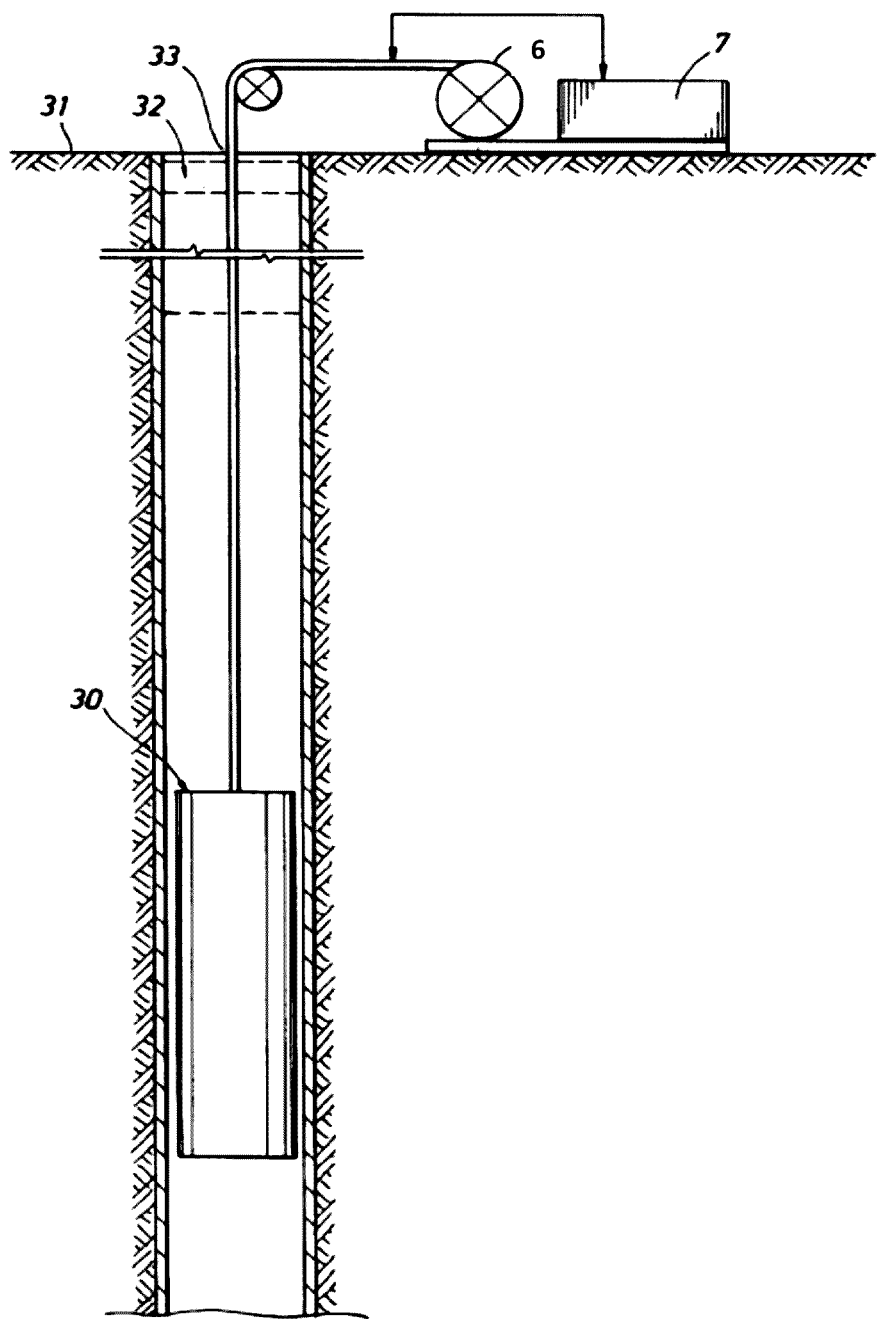
FIG. 1A is a schematic diagram of a subterranean wireline well logging system.
Figure 1B:
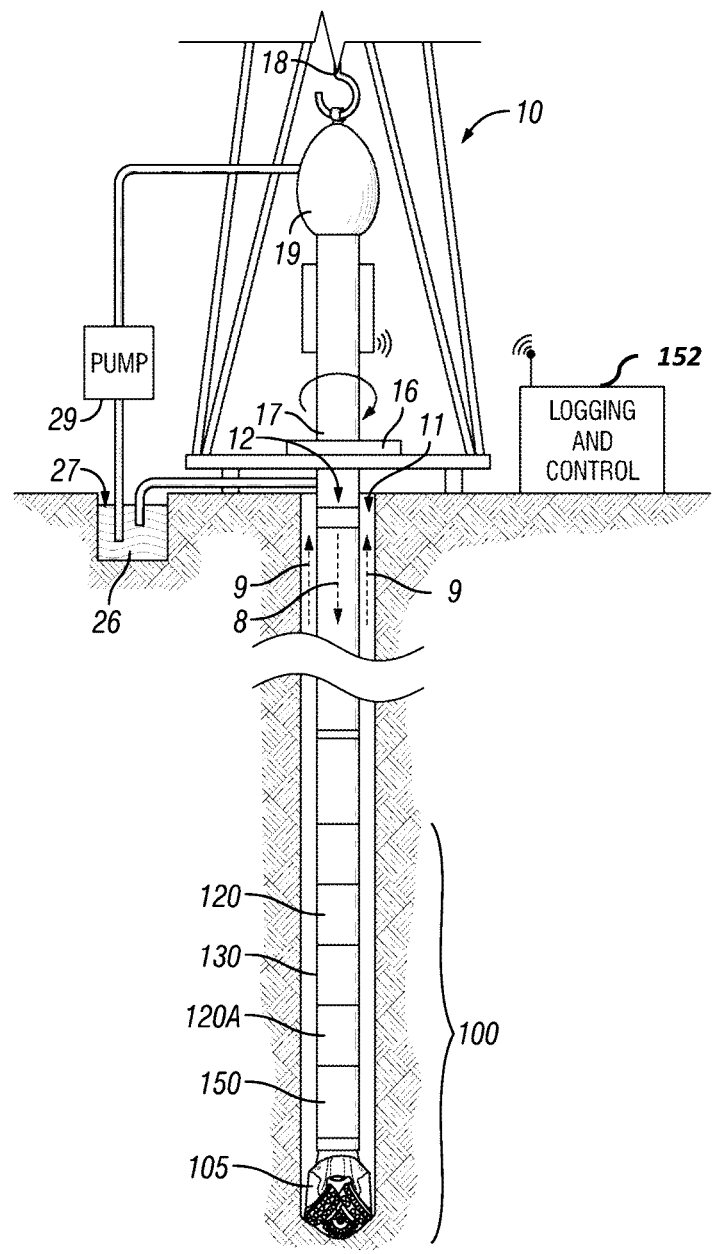
FIG. 1B is a schematic diagram of a subterranean logging-while-drilling and/or measurement-while-drilling well logging system.

To provide some general background with respect to the field of well logging and formation evaluation, FIGS. 1A and 1B illustrate different types of well site systems, which can be deployed onshore or offshore. Specifically, FIG. 1A illustrates a wireline system for investigating earth formations. As shown, the system includes a nuclear magnetic resonance (NMR) logging device 30 for investigating earth formations 31 traversed by a borehole 32. The NMR logging device 30 is suspended in the borehole 32 on an armored cable 33 (e.g., a wireline cable), the length of which substantially determines the relative axial depth of the device 30. As can be appreciated, the cable length is controlled by suitable means at the surface such as a drum and winch mechanism 6. Surface equipment 7 can be of conventional types and can include a processor-based system which communicates with downhole equipment including NMR logging device 30. The NMR logging device 30 may include a permanent magnet or magnet array that produces a static magnetic field in the formations, and one or more radio frequency (RF) antenna for producing pulses of magnetic field in the formations and for receiving the spin echoes from the formations. A variety of downhole NMR logging tools are known in the art, including the type disclosed in U.S. Pat. No. 4,710,713.

FIG. 1B shows another example of another type of well site system for logging-while-drilling (LWD) and/or measurement-while-drilling (MWD) applications. Here, a borehole 11 is formed in subsurface formations by rotary drilling in a manner that is well known. Some embodiments can also use directional drilling. As shown, a drill string 12 is suspended within the borehole 11 and has a bottom hole assembly (BHA) 100 which includes a drill bit 105 at its lower end. The surface system includes platform and derrick assembly 10 positioned over the borehole 11, with the assembly 10 including a rotary table 16, kelly 17, hook 18 and rotary swivel 19. In operation, the drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could alternatively be used.

In this example embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this manner, the drilling fluid lubricates the drill bit 105 and carries formation cuttings up to the surface as it is returned to the pit 27 for recirculation.

The BHA 100 of the illustrated embodiment includes a logging-while-drilling (LWD) module 120, a measuring-while-drilling (MWD) module 130, a rotary-steerable system and motor 150, and drill bit 105. The LWD module 120 may be housed in a special type of drill collar, as is known in the art, and can contain one or more types of logging tools. It will also be understood that more than one LWD and/or MWD module can be employed, as represented at 120A. The LWD module includes capabilities for measuring, processing, and storing information, as well as for communicating with the surface equipment. In the present embodiment, the LWD module includes a NMR measuring device.

The MWD module 130 is likewise housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid 26, although other power and/or battery systems may also be employed. By way of example only, the MWD module 130 may include one or more of the following types of measuring devices: a weight-on-bit measuring device, a torque measuring device, a vibration measuring device, a shock measuring device, a stick/slip measuring device, a direction measuring device, and an inclination measuring device. The operation of the assembly 10 of FIG. 1B may be controlled using the logging and control system 152, which may include one or more processor-based computing systems. In the present context, a processor may include a microprocessor, PLC, FPGA, ASIC, SOC, or any other suitable integrated circuit capable of executing encoded instructions stored, for example, on tangible computer-readable media.

As discussed above, while many well logging tools are available for fluid typing and the prediction of near wellbore reservoir fluid volumes, the accurate prediction of reservoir properties (e.g., composition, fluid density, molecular composition, saturates, aromatics, resins, and asphaltene (SARA) fractions, gas-oil ratio (GOR), etc.) using NMR techniques has been a continuing challenge for the industry. For example crude oils encountered in reservoirs are usually complex and variable mixtures of organic and inorganic molecules containing different amounts and types of dissolved gas molecules which cannot be accurately described by the simple idealized models commonly used in the industry. Accordingly, it was determined that accurate prediction of fluid properties from NMR could be better addressed using a model-independent approach to address the inherent complexity of crude oils. One aspect of this approach is to provide a database of NMR, PVT, and physical properties data acquired on live oils at realistic reservoir conditions (e.g., up to 25 kpsi and 175 C or more). However, the development of such a database has been challenging due to the limitations of existing commercial NMR measurement systems in laboratory settings, i.e., many commercial NMR measurement systems cannot acquire measurements at pressures and temperatures typical of reservoir conditions and also lack sufficient SNR for reliable measurements.

Accordingly, the present disclosure relates to a high performance low field NMR system capable of making NMR measurements on live oils at pressures up to 25 kpsi and temperatures up to 175 C. The phrase "up to" in this regard is not intended to imply that 25 kpsi is an upper limit of pressure or that 175 C is an upper limit of temperature for the disclosed NMR measurement system. Rather, this is intended to mean that embodiments of the disclosed NMR measurement system are capable of acquiring measurements on live oils at least up to a pressure of 25 kpsi and at least up to a temperature of 175 C, although the system is not necessarily precluded from acquiring measurements above either or both of these thresholds. Rather, these thresholds are mentioned only as realistic environmental conditions typically encountered in oil reservoirs. Further, those skilled in the art will appreciated the term "live oil," as used herein, refers generally to an oil containing dissolved gas in solution. In contrast, a "dead oil" is one that contains substantially no dissolved gas at a sufficiently low pressure.

Embodiments of the disclosed NMR measurement system include an NMR spectrometer, a compact sensor having an NMR magnet with a low static magnetic field gradient, an RF antenna, and a pair of pulse filed gradient (PFG) coils which may be used for NMR diffusion measurements. The NMR spectrometer may have a proton Larmor frequency of approximately 2 MHz, which is near or above the operating frequencies of most NMR logging tools. It is worth noting that there is generally negligible frequency dependence for $T_1$ or $T_2$ below 2 MHz for crude oils having viscosities in the range typically sampled by fluid sampling tools. At higher frequencies significant frequency dependence occurs in $T_1$, which is observed to increase with frequency for crude oils containing asphaltenes at frequencies of 10 MHz and higher (See Zielinski et al., "*Nuclear Magnetic Resonance Dispersion of Distributions as a Probe of Aggregation in Crude Oils*," Energy & Fuels, vol. 25, pp. 5090-5099 (2011)).

The high performance NMR measurement system described herein has significantly improved signal-to-noise ratio compared to existing commercial systems. The NMR measurement system has been used to acquire a database of hundreds of NMR measurements at different temperatures and pressures on live oils. In accordance with embodiments of this disclosure, the database contains optical density and fluid properties data acquired on the same suite of oils at the same temperatures and pressures. Further, the NMR measurement system may be implemented in a laboratory setting, on a downhole tool, and/or in the field (e.g., a mobile surface measurement system).

The remainder of this disclosure is organized as follows. Section 2 discusses the various features of NMR measurement system, NMR pulse sequences, and the near infrared optics sensor, in accordance with one embodiment. Next, Section 3 discusses the process of generating a database of NMR measurements using the aforementioned NMR measurement system, as well as near infrared optics and fluid properties measurements on live oils samples. Finally, Section 4 discusses in more detail the use of the above-mentioned the model-independent mapping function method (Anand et al. 2012) to predict fluid properties from NMR measurements and discusses the accuracy of the prediction results. Section 4 also discusses what, if any, improvement in the accuracies of predicted fluid properties can be achieved by a joint inversion of the NMR and optics measurements.

Section 2: Nmr Measurement System 2.1 Design Limitations of Previous Low Field NMR Systems Existing commercial low field NMR spectrometers for high pressure and high temperature applications include a pressure cell made of a non-metallic material (e.g., ceramic). The radio frequency (RF) coil for transmitting and receiving NMR signals is usually situated outside the pressure cell. The pressure on the inner walls of the cell is offset by a pressurized fluid (invisible to NMR) contained outside the cell. This pressurized fluid reduces the pressure on the inner walls of the pressure cell and can also be heated to regulate the temperature of the sample. However, this design has a number of disadvantages.

First, due to the low filling factor (e.g., the fraction of the sensor volume that is occupied by the sample), a relatively poor signal-to-noise ratio (SNR) (e.g., about 15:1 in some cases) per acquisition is obtained. As a result, the measurements need to be repeated many times and averaged in order to provide reliable data and, therefore, the measurements take a very long time (e.g., 12 hours or more for a pulsed field gradient measurement at a given pressure and temperature) (See Winkler et al., "*The Limits of Fluid Property Correlations Used in NMR Well Logging: An Experimental Study of Reservoir Fluids at Reservoir Conditions,*" 45th SPWLA Annual Logging Symposium Transactions (2004)). Second, many existing commercial systems use thermal exchange with a heated NMR-invisible (e.g., hydraulic) fluid to heat the sample under study. As will be appreciated, this is generally a very inefficient means of heat transfer and leads to a long thermal equilibrium time. Further, the time to reach equilibrium increases dramatically with the measurement temperature.

Additionally, the thermal exchange with the hydraulic fluid can lead to differential heating of the sample along its length and, consequently, to convection currents. These currents interfere with the NMR measurements, particularly diffusion measurements. Further, the operation and maintenance of the conventional NMR measurement systems is very complex. Particularly, many existing systems require multiple seals to isolate the pressurized hydraulic fluid and the fluid under study. If the seals fail, the two fluids can mix and contaminate each other, thereby ruining the measurement.

2.2 Design Features of the High Performance NMR Measurement System

In general, a central component of the embodiments of the NMR measurement system disclosed herein is a sensor assembly. The sensor assembly includes a sample holder which receives a sample for analysis/measurement (e.g., a live oil sample), a radio frequency (RF antenna), pulse field gradient coils, and a magnet assembly. This section will begin by first providing a general overview of the sensor assembly and then describing the various components in more detail.

In accordance with embodiments of the present disclosure, the sample holder (generally shown in FIGS. 2A and 2B) of the measurement system may be formed of a material that is capable of withstanding very high pressures (e.g., up to 36 kpsi) without pressure compensation. The metallic sample holder may be formed using a non-magnetic metallic alloy with high tensile strength. For example, in one embodiment, the sample holder may be formed using "MP35N," which is a nickel-cobalt-chromium-molybdenum alloy with tensile strength rated up to 300 kpsi. A radio frequency antenna is disposed within the sample holder and may include coils wound about a slotted frame, which may be formed from titanium in one embodiment. As will be discussed on further detail below, the slotted design of the frame is particularly useful in that allows for a current sample within the holder to be more efficiently flushed when a new sample is to be introduced. This helps to protect the new sample from contamination, thus providing more accurate NMR measurement data.

The sample holder is disposed between a pair of coil fixtures containing exterior gradient coils configured to provide for pulsed field gradient (PFG) measurements. The gradient coils produce a linear gradient in the sensitive volume by transmitting low frequency DC pulses which are negligibly attenuated by the metallic sample holder. The sample holder encapsulated by the coil fixtures is disposed inside the bore of a permanent magnet assembly (discussed in more detail below with reference to FIG. 2C) and thus has a relatively small background gradient in the sensitive volume. Further, this configuration allows for the RF antenna to be completely submerged in the fluid sample, thus leading to increased SNR, i.e., more than an order of magnitude higher than that of existing commercial low field NMR systems.

The above-described configuration allows for the sensor assembly of the NMR measurement system to be heated in an oven to the required measurement temperature without the need for heat transfer from another fluid. As used herein, the "sensor assembly" may refer to sample holder, the RF antenna, the pulse field gradient coils, and the magnet assembly, when fully assembled. Since the system can be uniformly heated in an oven, convection currents induced by temperature gradients are generally avoided. Still further, the presence of the metallic sample holder and titanium antenna frame reduces the quality factor (Q) of the RF antenna, thereby leading to a large frequency bandwidth of the antenna. This increased bandwidth enables the operation of the system over a wide range of temperatures without the need to retune the antenna to match the Larmor frequency as it decreases with increasing magnet temperature. Thus, when compared to the sensors conventional NMR measurement systems mentioned above, the NMR sensor assembly of the present disclosure is generally easy to maintain and allows straightforward integration with other sensors, e.g., optical sensors, as discussed in more detail below.

2.3 NMR Sensor Assembly

Additional details of the above-described components of the NMR sensor assembly are provided in this section. As discussed above, the NMR sensor assembly includes a sample holder, an RF antenna, pulse field gradient coils, and a magnet assembly.

Figure 2A:
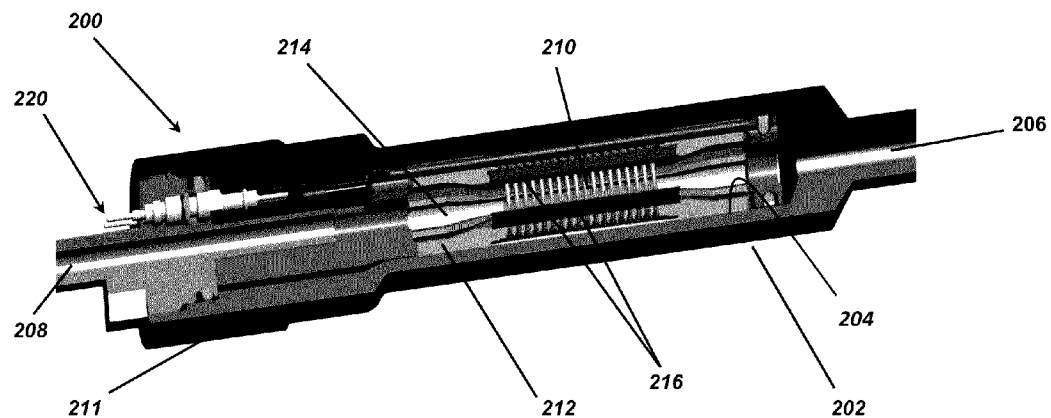
FIG. 2A is a cutaway view of a sample holder of an NMR measurement system in accordance with one embodiment of the present disclosure.
Figure 2B:
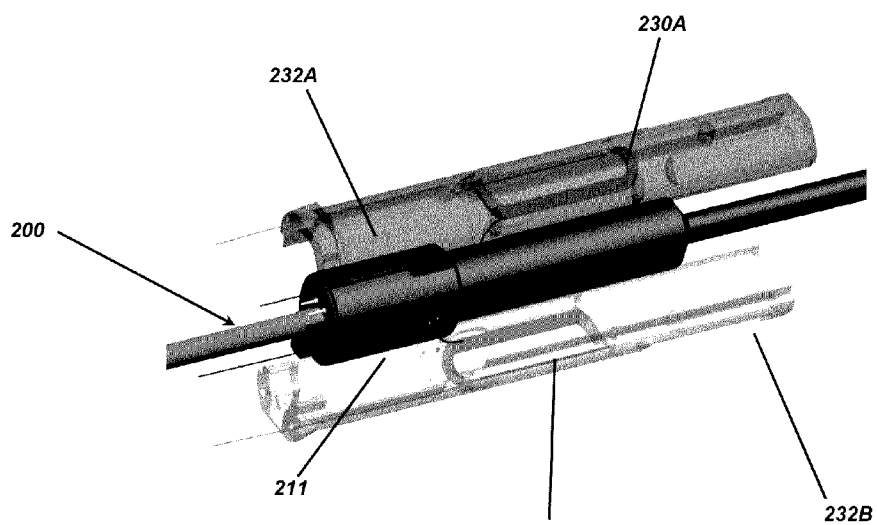
FIG. 2B shows how the sample holder of FIG. 2A is assembled between a pair of pulse field gradient coils in accordance with one embodiment of the present disclosure.

With reference to FIGS. 2A and 2B, certain components of a sensor assembly that may form part of the disclosed NMR measurement system are shown. Specifically, FIG. 2A shows a cutaway view of a sample holder 200 while FIG. 2B shows how sensor assembly is assembled with the sample holder 200 being disposed between two fixtures containing pulse field gradient coils. The sample holder 200 includes a body or housing 202 that defines an interior cavity 204 for receiving a sample. The body includes openings 206 and 208, which may define an inlet and outlet, respectively (or vice versa). Thus, a sample may be introduced into the cavity 204 via the inlet 206 and removed via the outlet 208. As will be appreciated, fluid control devices (not shown in FIGS. 2A and 2B) may control the entry of a fluid sample into and out of the sample holder 200. In the present embodiment, the body 202 of the sample holder 200 is generally cylindrical in shape and defines a generally cylindrical interior cavity 204. However, the body 202 and its corresponding cavity 204 may have different geometries on other embodiments (e.g., geometries with quadrilateral or elliptical cross-sections).

As shown, the body 202 of the sample holder 200 houses an RF antenna 210, represented in FIG. 2A as a solenoid coil. As discussed above, the body 202 of the sample holder 200 may be formed from a high tensile strength metal alloy, such as MP35N. The material for the body 202 may be selected based on high tensile strength and resistance to corrosion by reservoir fluid samples. In an embodiment where MP35N is used as the material for the body 202, the magnetic permeability of the sample holder 200 was found to be sufficiently low (e.g., $\mu$, of approximately 1.001) so that any disturbance in the magnetic field homogeneity in the sensitive region is generally negligible. As used herein, the "sensitive region" is understood to refer to the region within the RF antenna coil, as well as the vicinity just outside of the antenna coil where NMR signals are still detectable. In one embodiment, the diameter of the cylindrical interior cavity (the inside diameter (ID)) may be between approximately 0.5 and 1 inches (e.g., 0.65 inches in one particular embodiment) at the center of the sample holder 200, while the outside diameter (OD) may be between approximately 0.75 and 1.5 inches (e.g., 0.875 inches in one particular embodiment). Further, in one embodiment, the sample holder 200 may have a length of between approximately 10 and 20 inches (e.g., 10.83 inches in one particular embodiment). In the depicted embodiment, the sample holder 200 includes an end cap 211 coupled to one end of the body 202. For example, the end cap 211 may be threaded onto to the body 202. The end cap 211 may be formed from a metal alloy, such as a nickel-based super alloy sold by Special Metals Corporation of Hartford, N.Y., under the trade name Inconel™. As will be appreciated, the sample holder 200 and its associated components may be formed using any suitable manufacturing process (e.g., machining, CNC, etc.).

In the present embodiment, the RF antenna 210 includes a solenoid coil that is wound about a frame 212 which, as discussed above, may be formed of a non-magnetic metal such as titanium. Since the frame 212 is non-magnetic, it prevents distortion of the homogeneity of the static magnetic field in the sensitive volume. In one embodiment, the RF antenna coil 210 may have an axial length of between approximately 1 and 2 inches (e.g., 1.5 inches in one particular embodiment) and a coil diameter of between approximately 0.25 and 0.5 inches (e.g., 0.38 inches in one particular embodiment). The sample holder 200 may have a measurement volume of between approximately 5 and 15 cubic centimeters (cc) (e.g., approximately 8 cc in one particular embodiment). In the present embodiment, approximately 80 percent of the NMR signal may come from the fluid located in the space inside the antenna coil 210 (i.e., commonly referred to as the "sweet spot") while the remainder of the NMR signal is from the fluid in the annular region between the antenna coil 210 and the sample holder 200. Because the antenna coil 210 is completely surrounded by the sample fluid, this design results in an NMR fill factor of greater than 1, which greatly enhances the SNR of the measurements when compared to certain conventional NMR measurement systems. For instance, an SNR of approximately 100:1 to 250:1 or greater were found to be achievable using such a system.

As discussed briefly above and further shown in FIG. 2A, the frame 212 includes one or more slots 214 oriented longitudinally (relative to the longitudinal axis of the body 202). This slotted configuration provides for fluid communication between the fluid inside the RF antenna coil 210 and the fluid outside the coil 210. Accordingly, when a new sample is to be introduced into the sample holder 200, the slotted design of the frame 212 allows for the current sample to be flushed more efficiently flushed from the sample holder 200 (and particularly from the sensitive region) to allow for the entry of the new sample. This increased flushing efficiency of the measurement volume is helpful in obtaining non-contaminated samples during the live oil charging procedure (discussed further below), which ultimately improves the accuracy of the NMR measurement data. While the flushing efficiency is greatly improved compared to conventional measurement systems, as a best practice, it may be useful to fill and flush the sample holder 200 several times (e.g., 2 or 3 times) when a new sample is being introduced to ensure minimal contamination of a fluid sample (e.g., the old sample in the sample holder may be flushed and filled with fluid corresponding to the new sample, and the new sample may be flushed and refilled with more of the new sample several times). As also shown in FIG. 2A, the antenna 210 inside the sample holder 200, and the antenna 210 and the accompanying frame 212 may be secured within the interior cavity 204 by a set of retaining springs 216. Moreover, the electrical connection to the antenna 210 is provided by the electrical connectors 220, which include pressure feed-through pins in the illustrated embodiment. Further, though illustrated as longitudinal slots, it should be appreciated that the slots 214 may be oriented transversely with respect to the axis of the body 202 in some embodiments, or may be oriented neither transversely or longitudinally in other embodiments.

The sensor assembly also includes a pair of pulse field gradient coils 230 (referred to separately as 230A and 230B in FIG. 2B). The gradient coils 230 are used to create a magnetic field gradient in the sensitive region for pulsed field gradient (PFG) diffusion measurements. In the illustrated embodiment, the gradient coils 230 are provided as elliptically shaped Maxwell pairs which are embedded in respective coil fixtures 232 (referred to separately as 232A and 232B in FIG. 2B). As will be appreciated, the coils 230 may have other shapes and geometries in other embodiments. When assembled, the sample holder 200 is disposed between the fixtures 232A and 232B (e.g., in a "sandwiched" manner). In one embodiment, the coil fixtures 232 may be formed from a thermoplastic material, such as polyether-ether-ketone (PEEK). In operation, the gradient coils 230 carry current in opposite directions and create a linear magnetic field gradient in the measurement volume of the sample holder 200. In one embodiment, the coils 230 may be arranged in a geometric shape (e.g., elliptical in the illustrated embodiment) having a length of between approximately 2 and 4 inches (e.g., 2.6 inches in one particular embodiment) and a width of between approximately 0.5 and 1.5 inches (e.g., 0.75 to 0.8 inches in one particular embodiment). Further, in the present embodiment, the gradient coils 230 may be arranged such that they are diametrically opposed about the sample holder 200. In a further embodiment not shown in FIG. 2B, the gradient coils 230 may be located inside the sample holder 200 (e.g., inside the cavity 204), or may be embedded in the wall of the sample holder 200.

When assembled, the sample holder 200 and gradient coils 230 (with their respective fixtures 232) fit inside a bore of a permanent magnet assembly used for NMR measurements. The magnet assembly will be discussed in more detail below with reference to FIG. 2C. The low frequency PFG pulses are negligibly attenuated by the metal sample holder 200. However, the PFG pulses may generate eddy currents in the sample holder 200, which can affect the phase of the NMR spin echoes. The effect of such eddy currents was observed and investigated during experimentation, and it was found that the effect of the eddy currents is generally negligible if the duration between gradient pulses and echoes is approximately 1.5 millisecond (ms) or greater.

In experimentation, a linear calibration between the current in the gradient coils 230 and the corresponding magnetic field gradient in the measurement volume was determined prior to performing diffusion measurements. The calibration was obtained at room temperature using bipolar diffusion editing pulse sequences with a fluid of known diffusivity, such as water. It was found that the bipolar PFG pulse sequence cancels the cross term containing the scalar product of the static magnetic field gradient of the NMR magnet and the applied pulsed field gradient. This bipolar PFG pulse sequence method is described in additional detail in commonly assigned U.S. Pat. No. 7,253,618 to Freedman et al., which is hereby incorporated by reference in its entirety. As will be appreciated, the cross term which is present in the conventional Stejskal-Tanner PFG sequence (e.g., a unipolar sequence) may introduce systematic errors in measured diffusion coefficients. The use of a bipolar sequence generally cancels the cross terms, thus mitigating such systematic errors (See Stejskal et al., "*Spin Diffusion Measurements: Spin Echoes in the Presence of a Time-Dependent Field Gradient*," Journal of Chemical Physics, vol. 42, pp. 288-92 (1965)).

The above-mentioned linear calibration was validated by using it the calibration to measure the diffusivity of water at multiple temperatures up to 175 C. The results were found to agree with the literature results described in Krynicki et al., "*Pressure and Temperature Dependence of Self-Diffusion in Water*," Faraday Discussion of the Chemical Society, vol. 66, pp. 199-208 (1978), to within approximately 4%. This essentially confirms that the calibration is temperature-independent and remains valid when used in real world reservoir conditions (e.g., up to 175 C). The accuracy of the PFG measurements was further validated by performing diffusion measurements with hexane at multiple temperatures and pressures for which the literature values of the diffusivity is known (See Harris, "*Temperature and Density Dependence of the Self Diffusion Coefficient of n-Hexane from 223 to 333K and up to 400 MPa*," Journal of the Chemical Society, Faraday Transactions 1: Physical Chemistry in Condensed Phases, vol. 78, pp. 2265-2274 (1982)). Again, it was shown that the results based on the PFG measurements of the present system are in agreement with the known literature values to with an accuracy of within 4%.

Figure 2C:
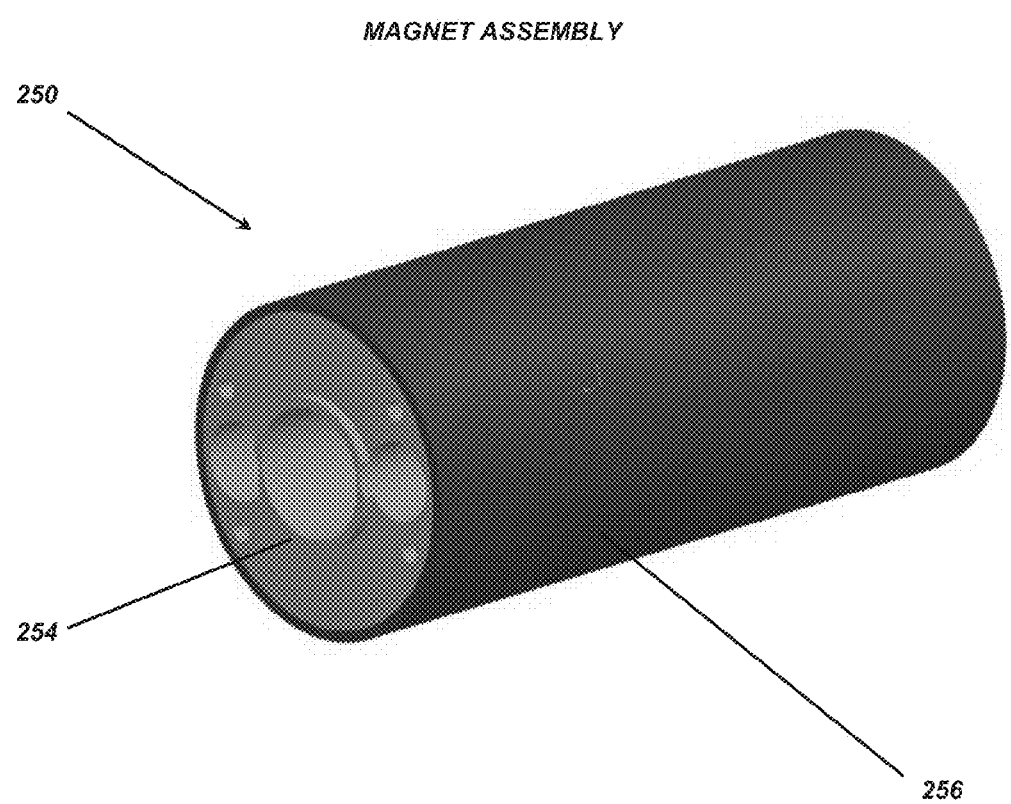
FIG. 2C shows an example of a magnet assembly in which the sample holder of FIGS. 2A and 2B may be disposed in accordance with one embodiment of the present disclosure.

FIG. 2C shows a magnet assembly 250 that may be part of the NMR measurement system in accordance with one embodiment. In this illustrated embodiment, the magnet 250 includes a samarium cobalt (SmCo) permanent magnet. The magnet 250 may have a field strength of between approximately 500 and 600 Gauss (G) at room temperature (e.g., approximately 535 G in one particular embodiment), which may correspond to a proton Larmor frequency of approximately 2.28 MHz. The magnet 250 also has a low static magnetic field gradient, which makes it ideal for use with the sensor assembly of the NMR measurement system of the present disclosure. For example, the static magnetic field gradient over the sample volume was measured at multiple temperatures from room temperature up to 175 C, and the average magnetic field gradient for this particular implementation was found to be less than 1 G/cm for all temperatures.

In the illustrated embodiment, the magnet assembly 250 is generally cylindrical in shape and may have a length of between approximately 6 and 18 inches (e.g., approximately 8 inches in one particular embodiment) and an outside diameter (OD) of between approximately 3 and 6 inches (e.g., approximately 3.6 inches in one particular embodiment). As further shown in FIG. 2C, the magnet 250 includes central bore 254. When the sensor assembly is fully assembled, the central bore 254 houses the sample holder 200 including the RF antenna and the gradient coils 230 in their respective fixtures 232. In one embodiment, the bore 254 may have a diameter of between approximately 2 to 4 inches (e.g., approximately 2.6 inches in one particular embodiment). As will be appreciated, the dimensions and geometry of the magnet assembly may depend on the dimensions of the sample holder 200.

In accordance with one embodiment, the magnet assembly 250 contains two spatially separated parallel plates which may be formed from non-magnetic stainless steel. For each plate there are situated SmCo magnets, each magnetized perpendicularly to the plate. The magnetic field variations in the measurement region between the plates are smoothed by magnetic pole pieces situated below and adjacent to each plate. This design, which is described in more detail in U.S. Pat. No. 7,683,613 to Freedman et al., results in creation of a magnetic field in a direction transverse to the axial direction of the sample holder 200 (when the sample holder 200 disposed in the bore 254). Here, the static magnetic field gradient in the measurement volume is relatively small (e.g., less than 1 G/cm), which enables accurate and precise measurements of the long $T_2$ values that may be observed in reservoir fluids. The magnet assembly 250 is contained in a cylindrical magnetic shell 256 which provides a return for the magnetic flux and also serves as shielding for radiation and/or noise.

Figure 3:
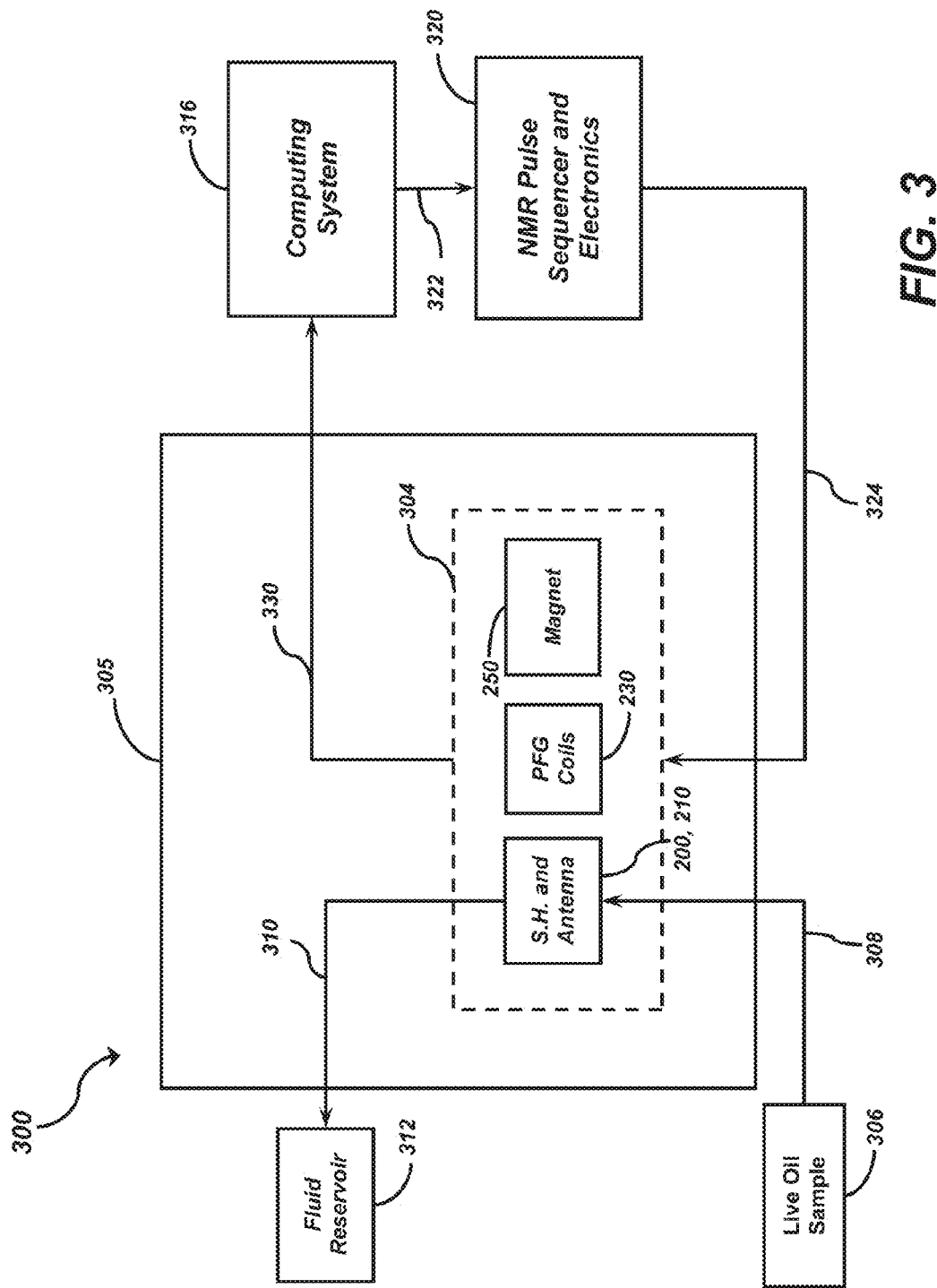
FIG. 3 is a simplified schematic block diagram showing an NMR measurement system that includes the sample holder and magnet assembly of FIGS. 2A-2C, in accordance with an embodiment of the present disclosure.

FIG. 3 is a simplified schematic block diagram showing the sensor assembly described above in the context of the NMR measurement system in accordance with one embodiment of the present disclosure. As shown, the NMR measurement system 300 includes the sensor assembly 304 having the sample holder 200 and antenna 210, the pulse field gradient coils 230, and the magnet assembly 250. In the present example, the sensor assembly 304 may be contained within a thermal control device 305. The thermal control device 305 allows for a live oil sample 306 to be heated to one or multiple temperatures at which NMR measurements are desired on the sample 306. By way of example, where the NMR measurement system 300 is set up in a laboratory setting, the thermal control device 305 may be a heating oven. The NMR measurement system 300 may also be implemented on a downhole tool, such as a downhole fluid sampling tool or formation evaluation tool. In such cases, other types of suitable thermal control devices 305 suitable for use on a downhole tool may be used, and the fluid sample 306 may represent a sample obtained directly from a formation, such as by using a probe or any other suitable fluid sampling device.

As seen in FIG. 3, the sample 306 may be introduced to the system 300 via the conduit 308. For example, the conduit 308 may be fluidly coupled to the opening 206 of the sample holder 200. When the sample holder 200 is filled with the sample 306, NMR measurements may be obtained at various temperatures and pressures. As used herein, the term "fill" or "filled" is understood to mean that a sufficient amount of the sample 306 has filled the volume of the sample holder 200 to enable the acquisition of NMR measurements. For example, a sufficient amount may be that which results in the antenna coil 210 being fully or at least partially submerged within the fluid sample 306. That is, "filled" in the present context is not necessarily limited to meaning that the volume inside the sample holder 200 is entirely occupied by the sample 306, but could mean sufficiently filled to a degree that enables accurate NMR measurements, (e.g., substantially filled, mostly filled, partly filled, or the like). Once measurements are completed, the sample 306 may be expelled to a fluid reservoir 312 by way of conduit 310, which may be fluidly coupled to the opening 208 of the sample holder 200. As discussed above, the slotted design of the antenna frame 212 (best shown in FIG. 2A) enhances the flushing efficiency of the sample holder 200, which helps to reduce fluid contamination when subsequent samples are being introduced.

For obtaining NMR measurements, the system 300 includes a computing system 316 and a pulse sequencer with associated electronics (referred to herein as "pulse sequencer") 320. As will be appreciated, the computing system 316 may include one or more processors (e.g., a microprocessor, FPGA, application-specific integrated circuits (ASICs), programmable logic device, SoC, etc.) and memory. The memory may include one or more non-transitory computer-readable media (such as a hard drive, ROM, optical drive, solid state storage, etc.) that may store programmed instructions for providing digital instructions 322 to the pulse sequencer 320. The computing system 316 may include one or more input devices (e.g., a keyboard and/or mouse, touchscreen input, etc.) and one or more output devices. For instance, one output device may include a display capable of displaying a graphical user interface, thus allowing a user to interact with the computing system 316, such as for providing inputs to cause the computing system 316 to generate instructions 322 that will cause the pulse sequencer 320 to generate the desired pulse sequences 324 for NMR measurements. Additional details regarding the NMR pulse sequences are discussed in the following Section 2.4.

The pulse sequences 324 generated by the pulse sequencer 320 are provided to the sensor assembly 304, and NMR measurements may be obtained on the fluid sample 306 as it resides in the sample holder 200. The resulting NMR measurements 330 may be transmitted back to the computing system 316 for additional processing and for storage. In one embodiment, the computing system 316 may be configured to execute instructions that predict the fluid properties of the sample 306 based on the received NMR measurements 330. For example, as will be described in more detail below, the prediction of fluid properties in this manner may use a radial basis function (RBF) mapping function in conjunction with a database containing known measured fluid properties, NMR measurements, as well as other types of measurements (e.g., optical measurements).

2.4 NMR Pulse Sequences

In addition to the sensor assembly 304 described above in FIGS. 2-3, the NMR measurement system 300 of the present disclosure includes a fully programmable pulse sequencer 320 and is capable of performing generally all standard low field NMR relaxation time and diffusion measurements. A live oil database was constructed to include $T_1$, $T_2$, and diffusion (D) measurements made on a number of live oil samples at various temperatures and pressures. In this experiment, the measurements types performed to acquires this data were as follows: (1) Carr-Purcell-Meiboom-Gill (CPMG) measurements of $T_2$, (2) saturation recovery/CPMG for simultaneous measurement of $T_1$ and $T_2$, and (3) bipolar PFG/CPMG for simultaneous measurement of diffusion (D) and $T_2$. In this particular experiment gain correction hardware was not use in conjunction with the NMR measurement system 300 (thus hydrogen index (HI) measurements on the live oil samples were not made). However, it should be appreciated that gain correction hardware could be included as part of such a system, and thus hydrogen index (HI) measurements can also be made using this system 300 (e.g., by the antenna coil 210).

In acquiring the aforesaid measurements, the CPMG acquisitions were Phase Alternated Pairs (PAP) used to eliminate DC offsets as well as any ringing caused by the 180 degree pulses. The wait time preceding each CPMG measurement, in this experiment, was at least 5 times the maximum longitudinal relaxation time in the fluid sample. The saturation recovery/CPMG sequences included a suite of PAP echo trains that were acquired using different recovery times. Prior to each recovery time, the longitudinal magnetization was driven towards zero by application of a series of 90 degree RF pulses with a few spoiler gradient pulses. Following each recovery time, a CPMG echo train was acquired. In this particular experiment, a suite of measurements typically included about 12 recovery times selected to be equally spaced on a logarithmic scale. This suite of measurements was simultaneously inverted to produce a two-dimensional $T_1$-$T_2$ map.

As briefly mentioned above, the Stejskal-Tanner PFG technique is a conventional unipolar PFG pulse sequence that is commonly used in the industry to measure molecular diffusion coefficients for liquids. However, due to the configuration of the sensor assembly 304, using the Stejskal-Tanner PFG sequence, a cross term containing the scalar product of the static magnetic field gradient of the magnet 250 and the applied pulsed field gradient from the pulse field gradient coils 230 is introduced. This cross term can introduce systematic errors into the measured diffusion coefficients. Accordingly, embodiments of the NMR measurement system may use a bipolar PFG pulse sequence, as described above, to obtain accurate measurements of diffusion (D) and diffusion-free measurements of $T_2$ in the presence of the static gradient of the NMR magnet 250. This is because the bipolar sequence cancels out the cross terms.

Figure 4:
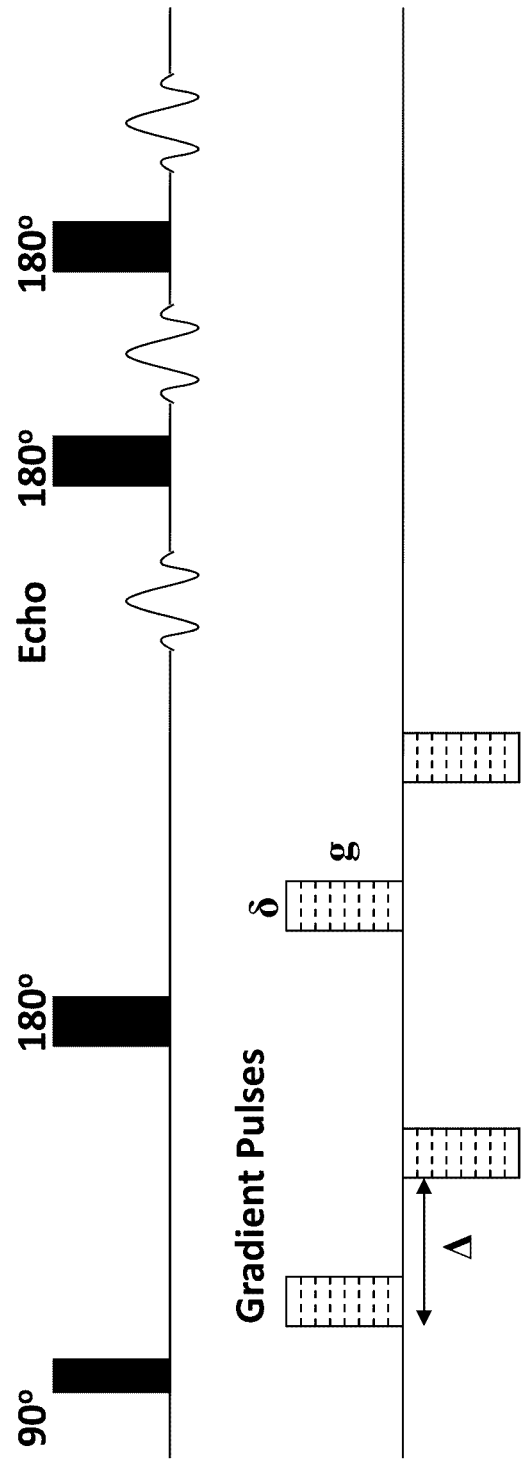
FIG. 4 is a graph showing an example embodiment of a bipolar pulse field gradient sequence that may be used to measure molecular diffusion distributions.

An example of a suitable bipolar PFG sequence that may be used with the described system is shown in FIG. 4. Here, it can be seen that four gradient pulses are applied before the diffusion-encoded spin-echo is observed. The diffusion-encoded spin-echo is refocused by a applying a train of 180 degree pulses to produce a sequence of spin-echoes whose amplitudes decay with relaxation time $T_2$. Further, it can be shown that the measurement kernel describing the bipolar PFG is the same as the kernel for a unipolar PFG except for an extra factor of two, which results from the application of four gradient pulses (as shown in FIG. 4) instead of two. This is further described in the above-referenced '618 patent to Freedman et al.

In the present example, two-dimensional diffusion and relaxation time measurements were based upon a suite of PFG sequences. The different PFG sequences within a suite were acquired using different gradient pulse widths (δ), gradient amplitudes, and diffusion times (Δ) to vary the diffusion attenuation. This suite of PFG measurements was then simultaneously inverted to produce a two-dimensional D-$T_2$ map, examples of which are described in more detail in commonly assigned U.S. Pat. No. 7,053,611 to Freedman, which is hereby incorporated by reference in its entirety.

2.5 Optics Sensor

In accordance with one embodiment of the NMR measurement system, an optical sensor may be provided to measure optical absorption, i.e. near infrared (NIR) absorption spectra, of live crude oils at reservoir conditions. Such a sensor may include an optical cell rated to withstand realistic reservoir conditions (e.g., up to at least 175 C and 25 kpsi). The sensor may be installed in the sample flow path in order to measure NIR absorption. In one example experiment, the optical cell is secured against the body of a heating apparatus used to heat the sensor assembly (and consequently the sample fluid contained therein), such as an oven. Securing the optical cell in this manner helps to prevent artifacts in the data that may occur as a result of oscillations and/or vibrations. In this experiment, the absorption spectra of live oils was measured in the wavelength range from approximately 400 nm to 2200 nm in increments of 1 nm. The spectrum was measured at each temperature and pressure for which the NMR measurements were made. The baseline spectrum of the optical cell, measured with pressurized $N_2$ at 500 psi and at the corresponding temperature, was subtracted from the absorption spectrum of the live oil to remove the absorption contribution from the cell. Accordingly, the optical density is defined as the logarithmic ratio of the incident ($I_o$) and transmitted ($I_t$) light intensities. Section 4 below provides a discussion on how this optical density data was combined with live oil NMR measurements to determine whether such a process would improve the accuracy of the NMR measurements on live oil samples.

Section 3: NMR, Optical Density, and Fluid Property Measurements

An extensive database of NMR, optical density, and fluid property measurements was acquired on a suite of 18 live oils at multiple temperatures and pressures. In order to include live oils with a wide range of fluid properties (such as viscosity, GOR, and SARA fractions) in the database, the oil samples were obtained from petroleum reservoirs in geographical locations around the world including the North Sea, Canada, United States, Gulf of Mexico, Middle East, Alaska, Malaysia, and Africa. Measurements were made over a wide temperature and pressure range to analyze the properties at representative reservoir conditions. The following subsections describe in detail a procedure for charging live oil samples using the NMR measurement system as well as the database of fluid property, NMR and optical density measurements.

3.1 Sample Charging

In the experiment described below, the live oil samples were prepared by equilibrating the samples for a period ranging from one to five days in a pressure cell at a known gas-oil ratio. The NMR and optical sensors were installed inside a heating oven while the electronics were kept outside of the heating oven. Metal flow conduits (referred to herein as "flowlines") are provided to connect the NMR sample holder 200 and the optical cell to inlet and outlet valves mounted on the outside of the oven. Using this set up, the fluids were injected into the NMR measurement system through the inlet valve using a hydraulic pump, while the outlet port is used to collect the effluents. These valves and pumps may constitute the flow control devices mentioned above with reference to FIG. 2A.

On technique for charging the live oil sample in accordance with aspects of the present disclosure includes the following steps. The NMR and optical sensors are heated inside the oven to the desired measurement temperature until thermal equilibrium is established. The flowlines are evacuated and purged with a pressurized gas, such as nitrogen ($N_2$) to generally remove any traces of fluid. Subsequently, a pressurized buffer fluid (e.g., pressurized at 10K psi) is injected into the flowlines through the inlet port. In one example, the buffer fluid is a dead stock-tank oil (STO) used to synthesize a live oil. The buffer fluid is used to maintain the flowlines and in the NMR sample holder 200 at pressures above the bubble point pressure of the live oil. In the present example, at least two fluid system volumes of live fluid are injected adiabatically into the system, whereby the buffer fluid is expelled as the live fluid is introduced into the system.

The sample charging process described above was validated, prior to acquisition of the database, as follows. A typical database live oil was selected and time-lapsed NMR D-$T_2$ measurements were performed as the STO buffer fluid was gradually flushed by the live oil. These measurements were performed to verify that the live oil would remain a single phase fluid during the charging procedure. The absence of a separate peak for free gas in the D-$T_2$ map confirmed that the live oil remained in a single phase during charging. The composition of the effluent at the outlet port was also measured after injecting fixed volumes of the live oil. It was further validated that the composition of the effluent exactly matched the composition of the live oil after injecting two system volumes.

3.2 Fluid Property Measurements

Having described the sample charging method, it is noted that a wide variety of fluid property measurements were made on the live oil samples in the database. Particularly, fluid properties that depend on temperature and pressure (e.g., density, viscosity, compressibility) were measured at three temperatures: 75 C, 125 C and 175 C, and at multiple pressures. Of course, it should be appreciated that other temperature points of interest could be measured in addition to or instead of the particular temperature points selected for the present experiment. In the present experiment the fluid property measurements were obtained using various measurement instruments in a laboratory setting. A brief description of the fluid property measurements is provided below.

Viscosity:

The viscosity of live oils was measured at the temperatures mentioned above using an electromagnetic viscometer. At each temperature, viscosity measurements were made at multiple pressures above the saturation pressure and up to 20 kpsi. While higher pressure settings may be used in other implementations, the upper limit in this particular experimental set up was constrained by the pressure rating of the specific viscometer used. Using this particular setup, the range of live oil viscosities included in the database covered almost three orders of magnitude, i.e., from 0.1 (centipoise) cp to 80 cp.

Fluid Density:

The density of the live oils was measured at the three temperatures and at multiple pressures using a densitometer rated to a maximum of approximately 20 kpsi. Of course, densitometers with higher pressure ratings could be used to obtain density measurements at pressures greater than 20 kpsi. Using this particular setup, the live oil densities were found to range from approximately 0.44 g/cc to 0.93 g/cc.

Molecular Composition:

Molecular composition was measured using gas chromatography (GC) techniques and devices. It was found that molar and weight fractions of components with carbon number ranging from C1 to C30 and higher were obtained using this particular setup.

Gas-Oil Ratio (GOR):

GOR was measured at standard conditions using a laboratory gasometer. In this particular setup, the GORs of the live oils used to populate the database was found to range from approximately 150 SCF/BBL to 3000 SCF/BBL.

Bubble Point:

The bubble point pressures of the single phase live oils were measured using a Constant Composition Expansion (CCE) instrument. The measurements of bubble point pressures were made at the three temperature points noted above: 75 C, 125 C, and 175 C.

Fluid Compressibility:

In general, isothermal fluid compressibility ($\beta$) measures the relative volume change of the live oil as a response to pressure change. Here, the fluid compressibility was measured using the CCE instrument at the three temperatures (75 C, 125 C, and 175 C) and at multiple pressures up to 20 kpsi.

Asphaltene Onset Pressure (AOP):

AOP is defined as the pressure at which asphaltenes precipitate from a live oil at a given test temperature while the pressure is decreased. In this particular setup, AOP was measured at the three temperatures (75 C, 125 C, and 175 C) using a solids detection system.

SARA Fractions:

SARA is defined as the fractions of saturates, aromatics, resins, and asphaltenes in dead oil. In this particular setup, SARA fractions were measured on dead oil versions (e.g., samples where the dissolved gas was allowed to escape) of the live oil samples using standard laboratory methods, as known to those skilled in the art.

3.3 NMR Measurements

Having described the types of fluid property measurements that were taken (as well as how they may be taken), the results of the NMR measurements on certain samples of live oils using the NMR measurement system is described in more detail in this section. As with the fluid property measurements, NMR measurements were performed on live oil samples at three temperatures: 75 C, 125 C, and 175 C. For each live oil sample and at each of these temperature points, NMR measurements were performed at multiple pressures above the bubble point and asphaltene onset pressures (AOP) of the live oil at that temperature. At 125 C and 175 C, measurements were performed up to a pressure of 25 kpsi. However, at 75 C, the maximum measurement pressure was generally limited to approximately 15 kpsi or 20 kpsi in some cases. As will be appreciated by those skilled in the art, the lower pressure limit at 75 C was used in this particular experiment because reservoirs at low temperatures are also typically at lower pressures.

Three types of NMR measurements were made at each temperature and pressure: CPMG, $T_1$-$T_2$ and D-$T_2$. The echo data was inverted to obtain $T_2$ distributions, and two-dimensional $T_1$-$T_2$ and D-$T_2$ maps. One-dimensional $T_1$ and D distributions were also obtained from the projections of the 2-D maps along the $T_1$ and D dimensions. In total, the database that was acquired included over 460 NMR measurements obtained on each of a sample set of 18 live oils at multiple temperatures and pressures. Results for a three particular oils from the sample set are described below for illustrative purposes.

Example Oil 1

A first live oil sample, referred to as "Oil 1" was obtained from a reservoir in the North Sea and has a relatively low GOR of approximately 207 SCF/BBL. The D-$T_2$ maps measured at the above mentioned temperatures and multiple pressures are shown in FIG. 5A. As shown, the peaks in the D-$T_2$ maps lie generally along the dead oil line, $$D = \lambda T_2, \quad (1)$$

where $\lambda = 5 \cdot 10^{-5}$ cm$^2$/sec$^2$. As can be seen in FIG. 5A, the D and $T_2$ values generally increase with temperature due to the increased mobility of the molecules as temperature increases. In contrast, D and $T_2$ generally decrease with pressure because of reduced mobility of fluid molecules under pressure. The pressure dependence of $T_2$ is also consistent with the increase in viscosity and rotational correlation time with the increase in pressure.

Figure 5B:
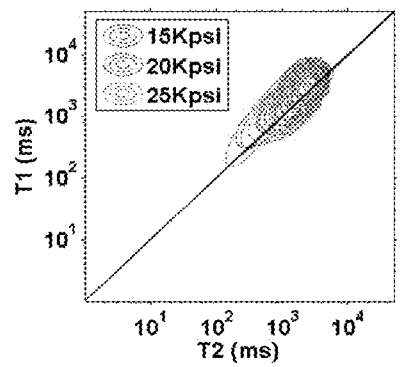

The $T_1$-$T_2$ maps for the oil at the corresponding temperatures and pressures are shown in FIG. 5B. The logarithmic mean $<T_1>$ and $<T_2>$ were also computed from the 1-D $T_1$ distribution and the diffusion-corrected $T_2$ distribution obtained from D-$T_2$ maps (FIG. 5A). It was found that the $<T_1>/<T_2>$ ratio is greater than unity, albeit not significantly, at all temperatures and pressures with the average value of approximately 1.3. Those skilled in the art will appreciate that it has previously been shown empirically that the deviation of $<T_1>/<T_2>$ ratio from unity in crude oils is caused by enhanced $T_2$ relaxation by paramagnetic atoms on the asphaltene molecules (See Zhang et al., "*Oil and Gas NMR Properties: The Light and Heavy Ends,*" 43rd Annual SPWLA Annual Logging Symposium Transactions: Society of Petrophysicists and Well Log Analysts (2000)). Here, the enhanced average value of 1.3 of the $<T_1>/<T_2>$ ratio for Oil 1 is indicative of the presence of asphaltenes. Laboratory analysis confirmed that Oil 1 contained approximately 1.5 wt % asphaltenes.

Example Oil 2

A second live oil sample, referred to as "Oil 2" was obtained from a reservoir in Africa and has a significantly higher GOR (approximately 1500 SCF/BBL) compared to Oil 1. FIGS. 6A and 6B show the D-$T_2$ maps and $T_1$-$T_2$ maps, respectively, obtained at multiple temperatures and pressures for Oil 2. Here, it can be seen that the peaks in the D-$T_2$ maps (FIG. 6A) for this sample lie generally to the left of the dead oil line (Equation (1)). This deviation arises because the dead oil line is based on the empirical correlation between diffusion and $T_2$ for dead oils and, therefore, does not take into account the enhanced diffusion due to the presence of gaseous components, such as methane and ethane, in live oils.

For Oil 2, the average $<T_1>/<T_2>$ ratio was found to be approximately 1.2, which is smaller than that for Oil 1. As can be appreciated, this observation suggests that Oil 2 contains smaller amounts of asphaltenes compared to Oil 1. This conclusion is consistent with the fact that the presence of greater quantities of non-polar gaseous components, such as methane, generally reduces the solubility of polar asphaltene molecules. Laboratory analysis confirmed that Oil 2 contained approximately 0.1 wt % asphaltene compared to 1.5 wt % contained in Oil 1.

Example Oil 3

Figure 7A:
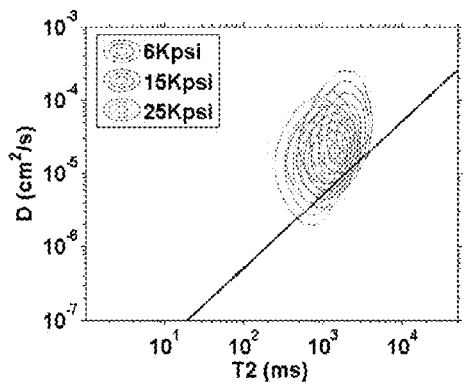

A third live oil sample, referred to as "Oil 3" was obtained from a reservoir in Colombia. This oil was found to have a moderate GOR (approximately 1053 SCF/BBL) compared to Oils 1 and 2 and contained approximately 0.08 wt % asphaltene content. FIGS. 7A and 7B show the D-$T_2$ maps and $T_1$-$T_2$ maps, respectively, obtained at multiple temperatures and pressures for Oil 3. As can be seen in FIG. 7A, the slopes of the peaks in the D-$T_2$ maps deviate significantly from the dead oil line. This deviation arises because paramagnetic atoms (such as nickel and vanadium) that are present in asphaltene molecules act as relaxation agents for the maltene molecules, thereby significantly reducing the $T_2$ relaxation times. However, it is understood that diffusion of maltenes is not significantly affected by the presence of asphaltenes. FIG. 7A shows that the slope of the peaks is independent of pressure at each of the measurement temperatures. However, it can be seen that the slope gradually decreases with increase in temperature. This observation suggests that the relaxation strength of the asphaltene molecules decreases with the increase in temperature. It is worth noting that the slope cannot necessarily be correlated with asphaltene content, contrary to the findings of Hurlimann et al., "*Hydrocarbon Composition from NMR Diffusion and Relaxation Data*," Petrophysics, vol. 50, pp. 116-129 (2009), on dead oils. This conclusion follows from the fact that Oil 1 has a higher asphaltene content than does Oil 3, but yet the D-$T_2$ maps for Oil 1 (FIG. 5A) generally exhibit a smaller slope.

The analysis of $T_1$-$T_2$ maps shows that the $<T_1>/<T_2>$ ratios for Oil 3 are larger compared to those for Oils 1 and 2. Furthermore, in contrast to Oils 1 and 2, the $<T_1>/<T_2>$ ratio for Oil 3 was found to decrease with temperature. To provide one example, in the present experiment, the average $<T_1>/<T_2>$ ratios for Oil 3 were found to be approximately 1.43 at 75 C, 1.37 at 125 C, and 1.32 at 175 C. This observed decrease in $<T_1>/<T_2>$ ratio is consistent with the above-stated conclusion that the relaxation strength of asphaltene molecules decreases with increase in temperature.

In summary, FIGS. 5A-7B illustrate that the temperature and pressure dependence of D and relaxation time distributions in crude oils is complicated and depends on the detailed molecular composition of the oil. Accordingly, this experiment shows that the use of previous physical models for interpreting diffusion and relaxation time measurements is insufficient, as physical models do not accurately represent the complex physics that govern molecular interactions.

3.4 Optical Density Measurements

Figure 8A:
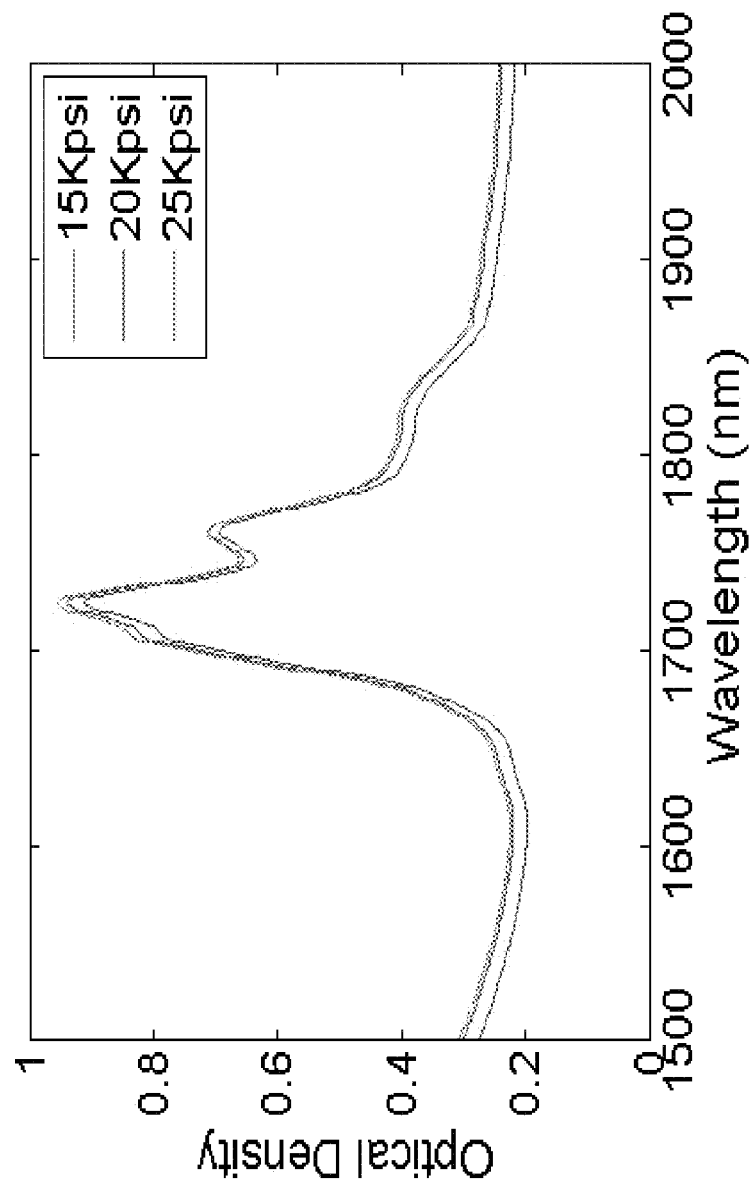
FIGS. 8A and 8B are graphs representing absorption spectra of the first live oil sample and the second live oil sample, respectively, based on optical measurements obtained therefrom at various pressures.
Figure 8B:
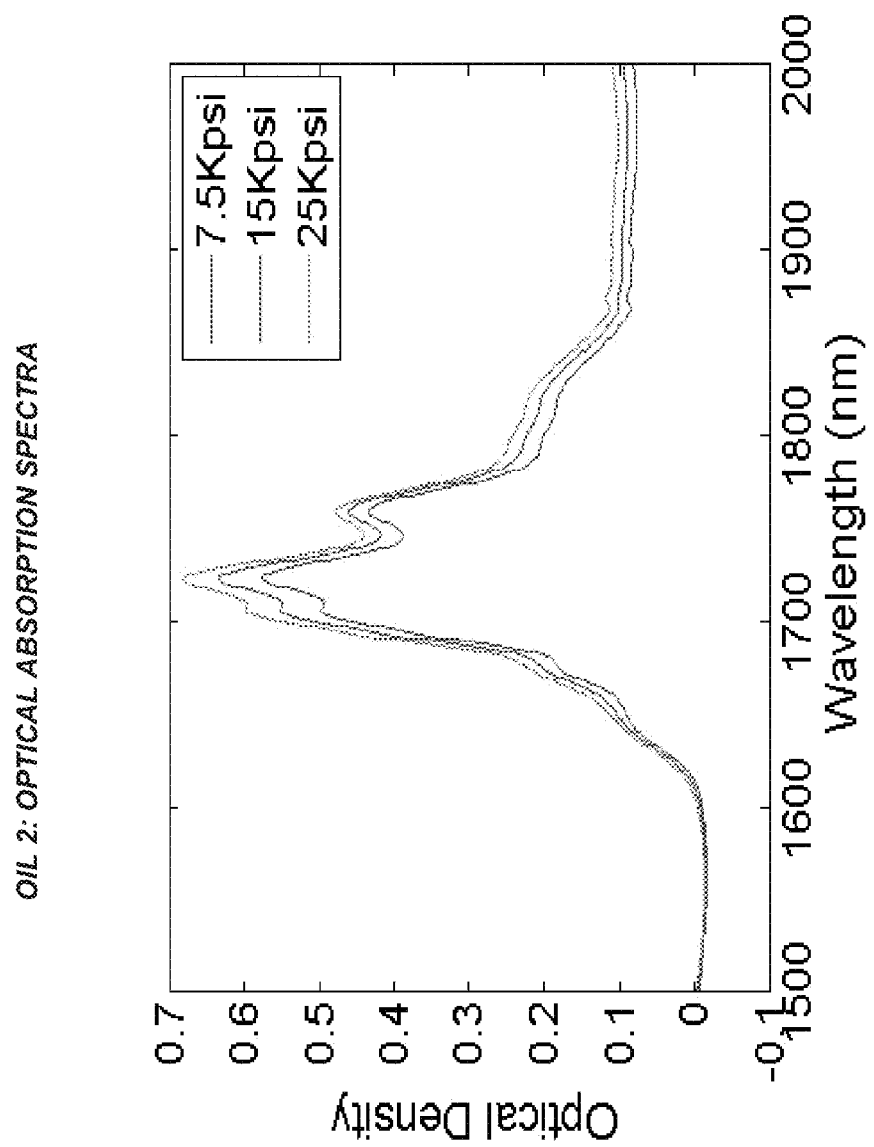

As part of the present experiment, optical density measurements were also obtained on some of the samples using the optical sensor discussed above in Section 2.5. FIGS. 8A and 8B show the optical absorption spectrum for Oil 1 and Oil 2, respectively, obtained at 175 C and at multiple pressures. The spectrum is shown in the NIR (near infrared) wavelength range from 1500 nm to 2000 nm. As can be seen, the molecular absorption peaks for both Oil 1 and Oil 2 at approximately 1700 nm, which corresponds to the resonance of the carbon-hydrogen (C—H) bonds. FIGS. 8A and 8B also show that the effect of increasing pressure is to increase the amplitude of the optical density without changing the shape of the absorption spectrum. As will be appreciated, the optical density increases with pressure due to the increase in the density of the oil as pressure increases. As discussed further below, one aspect of the present experiment included combining optical density measurements with NMR measurements to evaluate whether the use of optical density measurements in conjunction with NMR measurements helps to improve the accuracy of fluid property predictions using a RBF mapping-function technique.

Section 4: Method for Predicting Accurate Reservoir Fluid Properties

As discussed above, crude oils are complex mixtures including dissolved gases and various other hydrocarbon and inorganic molecules of unknown sizes, shapes, and types. The physics of such complex mixtures cannot be accurately described by simple idealized models, such as linear chain models or other physical models that do not account for the presence of aromatic, asphaltene, and other non-linear hydrocarbon molecules.

For the present experiment, a model-independent method, additional details of which are described in the above-referenced Freedman 2006 and Freedman et al. 2012 publications (both of which are incorporated herein by reference), was used to predict fluid properties of live oil samples based on the NMR measurements performed on these samples at the various pressures and temperatures stated above. When compared to previous methods and attempts at techniques for prediction of fluid properties (e.g., using physical models), the present model-independent method was found to be far more accurate in predicting the fluid properties of live oils.

The model-independent method uses the above-described database of NMR measurements and laboratory fluid properties measurements that were acquired on a representative suite of live oil samples (e.g., a total of 18 samples in this present experiment). The database is divided into input measurements such as NMR measurements, pressure, temperature, etc. and output measurements such as viscosity, density, molecular composition, SARA, etc. for each live oil sample. The unknown functional relationship between the input parameters and the outputs is then approximated by a general non-linear mapping function which is determined using the database.

This model-independent method was found to be flexible and allows, with relative ease, the combining of input measurements from multiple sensors, for example, NMR and optical sensors. The underlying principle of this model-independent method is that the physics is contained in the database and the unknown functional relationship between the input and output parameters can be approximated by a mapping function that is based on radial basis functions (RBFs). In one embodiment, the RBF may be a Gaussian RBF. Generally speaking, an RBF mapping function is able to accurately represent any smooth and continuous non-linear function. Further, such a mapping function is an analytical function which can be constructed from the database without iterative training and can be written as a linear combination of radial basis functions (RBF), as discussed in Freedman et al. 2012.

As an example embodiment, the RBF mapping functions used for predicting live oil properties in this particular study can be expressed in the general form:

$$\vec{F}(\vec{x}) = \frac{\sum_{i=1}^{N} \vec{c}_i \exp\left(-\frac{\|\vec{x}-\vec{x}_i\|^2}{2s_i^2}\right)}{\sum_{i=1}^{N} \exp\left(-\frac{\|\vec{x}-\vec{x}_i\|^2}{2s_i^2}\right)}. \quad (2)$$

Here, the mapping function $\vec{F}(\vec{x})$ represents the fluid property to be predicted, i.e., molecular composition, viscosity, density, SARA, etc. It should be noted that for multi-component oil properties, such as molecular composition, the mapping function is a vector having elements that represent the mole fractions of the different carbon numbers, whereas for single component oil properties, such as viscosity, the mapping function is a scalar function.

As can be appreciated, the summation expressions in Equation (2) are over the number of measurements N in the database. The database inputs for the i-th measurement are contained in the vector $\vec{x}_i$, and the vector $\vec{x}$ contains the input measurements made on an unknown sample of which the fluid properties are to be predicted. The expansion coefficients $\vec{c}_i$ can be determined from the database. When using a Gaussian RBF, the arguments of the Gaussian functions may be Euclidean distances in the input measurement space between the unknown input measurement vector $\vec{x}$ and the database input measurement vector $\vec{c}_i$ which can be expressed as follows:

$$\|\vec{x} - \vec{x}_i\|^2 = \sum_{k=1}^{N_c} (x_k - x_{k,i})^2, \tag{3}$$

where $N_c$ is the number of components in the vector of input measurements. The widths $s_i$ for the radial basis functions (e.g., Gaussian functions) can be determined from the nearest neighbor distances (discussed in more detail below), with $s_i$ being the width of the RBF corresponding to the i-th measurement.

4.1 Fluid Properties Predictions and Accuracies from NMR Measurements

Using the model-independent mapping function described above, various fluid properties were predicted. This subsection of the disclosure discusses the prediction of certain fluid properties and their accuracy when compared to the measured fluid properties.

Viscosity

The dependence of NMR relaxation in fluids on the fluid viscosity is generally well known for pure fluids. In that case, the relaxation rate is proportional to the ratio of the fluid viscosity ($\eta$) and the temperature, as shown in Equation (4) below:

$$\frac{1}{T_1} = \frac{1}{T_2} \propto \frac{\eta}{T}. \tag{4}$$

Those skilled in the art will appreciate that the above relationship is valid within the extreme narrowing regime for which the product of Larmor frequency and molecular rotational correlation time is significantly less than 1. Similarly, the diffusivity of spherical particles in a dilute solution is also related to the viscosity as can be expressed by the Stokes Einstein equation below:

$$D = \frac{k_B T}{6\pi \eta a_s}, \tag{5}$$

where $a_s$ is the radius of the diffusing spherical particles, $k_B$ is Boltzmann's constant, T is the temperature in degrees Kelvin, and $\eta$ is the viscosity of the solvent. The dependence of live crude oil viscosities on relaxation time and diffusivity distributions is, however, very complex and depends on the detailed molecular composition of the crude oil, temperature, and pressure. The existing empirical correlations used to predict live crude oil viscosities from NMR measurements have been based on simple alkane mixture models (See Lo et al., "*Correlations of NMR Relaxation Time with Viscosity, Diffusivity, and Gas/Oil Ratios of Methane/Hydrocarbon Mixtures*," SPE 63217, Society of Petroleum Engineers, presented at the SPE Annual Technical Conference and Exhibition (2000)). However, such simple empirical models do not accurately describe crude oils, which are complex mixtures with varying compositions.

However, the model-independent mapping function technique allows for accurate prediction of live crude oil viscosities from NMR measurements, thus overcoming many of the limitations of the aforesaid simple empirical models. As an example embodiment, the mapping function used in the present study to predict the live crude oil viscosities from NMR measurements (e.g., $T_1$, $T_2$ and D distributions), temperature, and pressure can be expressed in the form:

$$\eta = \frac{\sum_{i=1}^{N} c_i \exp\left(-\frac{\|\vec{A}_T - \vec{A}_{T,i}\|^2}{2s_i^2}\right)}{\sum_{i=1}^{N} \exp\left(-\frac{\|\vec{A}_T - \vec{A}_{T,i}\|^2}{2s_i^2}\right)}. \tag{6}$$

Here, $\vec{A}_T$ represents a vector that includes the amplitudes of the $T_1$ distribution $A(T_1)$, $T_2$ distribution $A(T_2)$, diffusivity distribution $\vec{A}_T$ temperature, and pressure of a live crude oil sample whose viscosity is to be predicted. For example, $A_T$ may be expressed as follows:

$$\vec{A}_T = \vec{A}_T(A(T_1), A(T_2), A(D), T, P). \tag{7}$$

In Equation (6), $\vec{A}_{T,i}$ is a vector that contains the inputs for the i-th sample in the database. A sample is defined by the database measurements made on a specific crude oil at a particular temperature and pressure. Further, the amplitudes of the $T_1$, $T_2$ and D distributions may be normalized with the respective largest values in the distribution to eliminate the dependency of the amplitudes on hardware and software settings. Temperature and pressure may be similarly normalized based on the largest respective values in the database. The dimensionality of the input vector is the sum of the number of components in the $T_1$, $T_2$ and D distribution plus two more for temperature and pressure. Additionally, the widths $s_i$ for the Gaussian functions, in one embodiment, may be computed to be proportional to the nearest neighbor distances in the database input, such as by way of the following equation:

$$s_i = \alpha(NN)_i, \tag{8}$$

where $(NN)_i$ represents the nearest neighbor Euclidean distance for the i-th sample in the database. As discussed in more detail below, the factor $\alpha$ in Equation (8) is a constant that can be determined using the database.

Figure 5B:
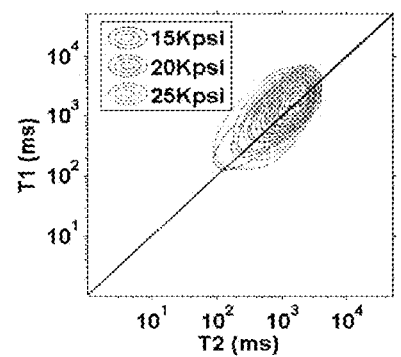
Figure 5B:
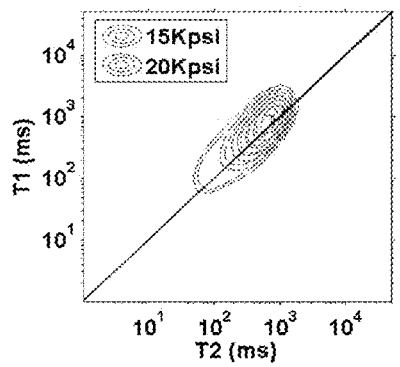
Figure 7A:
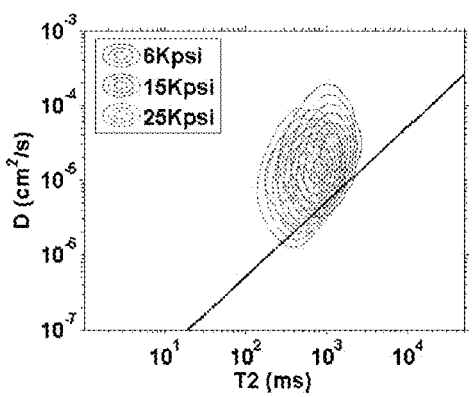
Figure 7A:
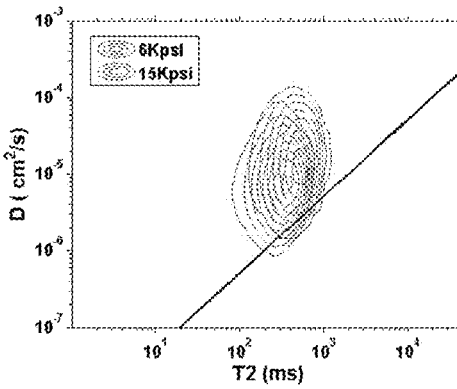

In the present study, the accuracy of the viscosity predictions was validated by applying the methodology to the database itself. Particularly, the validation was done using the "leave-one-out" method. In this method, the measurements at all temperatures and pressures made on each live oil are sequentially removed from the database, and a mapping function, i.e., Equation (6), is constructed between viscosity and input measurements for the remaining database samples. As each live crude oil was removed from the database, the predicted viscosities of the removed oil sample are obtained by way of the mapping function, i.e., Equation (2), using the input measurements that were made on this sample at the measurement temperatures (75 C, 125 C, 175 C) and pressures (e.g., ranging from 6 kpsi to 25 kpsi as indicated in FIGS. 5-7 above).

Figure 9:
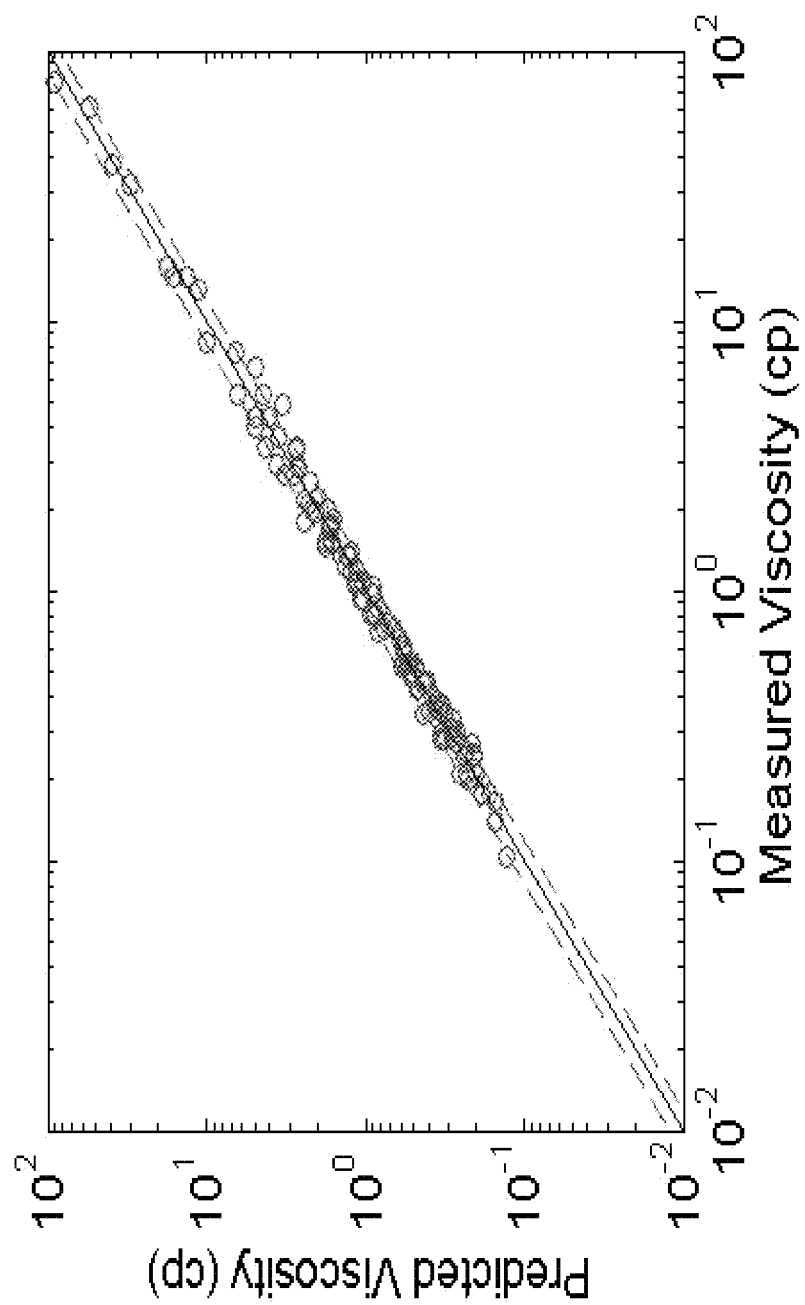
FIG. 9 is a graph that compares viscosity values predicted using a model-independent mapping function technique with measured viscosity values, in accordance with an aspect of the present disclosure.

It is noted that for this particular experiment, the NMR measurements made at pressures higher than 20 kpsi were not included in the database for the construction of the mapping function because the measured viscosity values were measured up to a maximum pressure of 20 kpsi (due to limitations in the pressure rating of the particular viscometer used). Furthermore, the measurements made on Oil 3 were also not included because the relaxation time distributions of this particular oil are more greatly affected by the presence of paramagnetic ions, as noted above (Section 3.3). Since this particular database did not contain other crude oils with such large concentration of paramagnetic ions, the NMR relaxation times for Oil 3 are not well represented by the remaining crude oils in the database. With the foregoing in mind, the viscosity predictions were obtained by using different combinations of $T_1$, $T_2$ and D distributions in the input vector. The accuracies of the results were comparable in all cases. However, it was observed that the most accurate predictions were obtained for the case in which the input vector consisted of normalized $T_1$ and D distributions, and normalized temperature (T) and pressure (P). FIG. 9 shows a graph comparing the predicted live crude oil viscosities with the viscosities measured in the laboratory. Specifically, the graph of FIG. 9 shows the comparison for predicted and measured viscosities for 113 measurements made on 17 live oils (with Oil 3 being excluded from the full set of 18 live oils) in the database. The solid line on the graph in FIG. 9 represents the best-fit line, and the dashed lines on either side of the solid line represent a 20% deviation.

For the viscosity analysis, an optimal a was determined using trial and error by minimizing the deviation between predicted and measured viscosities. In this particular experiment, the optimal value of a was found to be about 0.9. The viscosity predictions were found to be within an average accuracy of 10.6% over the entire viscosity range. Those skilled in the art will appreciate that this degree of accuracy is very good (e.g., when compared to previous model-based approached), especially when considering that there were no adjustable parameters in the estimation and the range of viscosity values covered almost three orders of magnitude. Additionally, since the diffusion distribution is generally not affected by the presence of paramagnetic ions, the viscosities of the live oil samples were also predicted using D distributions, temperature (T) and pressure (P) in the input vector (without $T_1$), with Oil 3 included in the database. In this case, predicted viscosities were found to be within an average accuracy of 12.7% over the entire range.

Density

The dependence of relaxation time and diffusivity of n-alkanes on the density has been studied extensively in the literature, i.e., von Meerwall et al., "*Diffusion of Liquid n-alkanes, Free-volume and Density Effects,*" Journal of Chemical Physics, vol. 108, pp. 4299-4304 (2004). Generally, the relaxation time and diffusivity of pure fluids decrease with density in a non-linear fashion. At the time of this experiment, to the best of the inventors' knowledge, the prediction of live crude oil density from NMR relaxation time and diffusion distributions had not previously been studied in this manner, and no reliable analytical or empirical models for the prediction of density from NMR measurements were known to exist.

Figure 10:
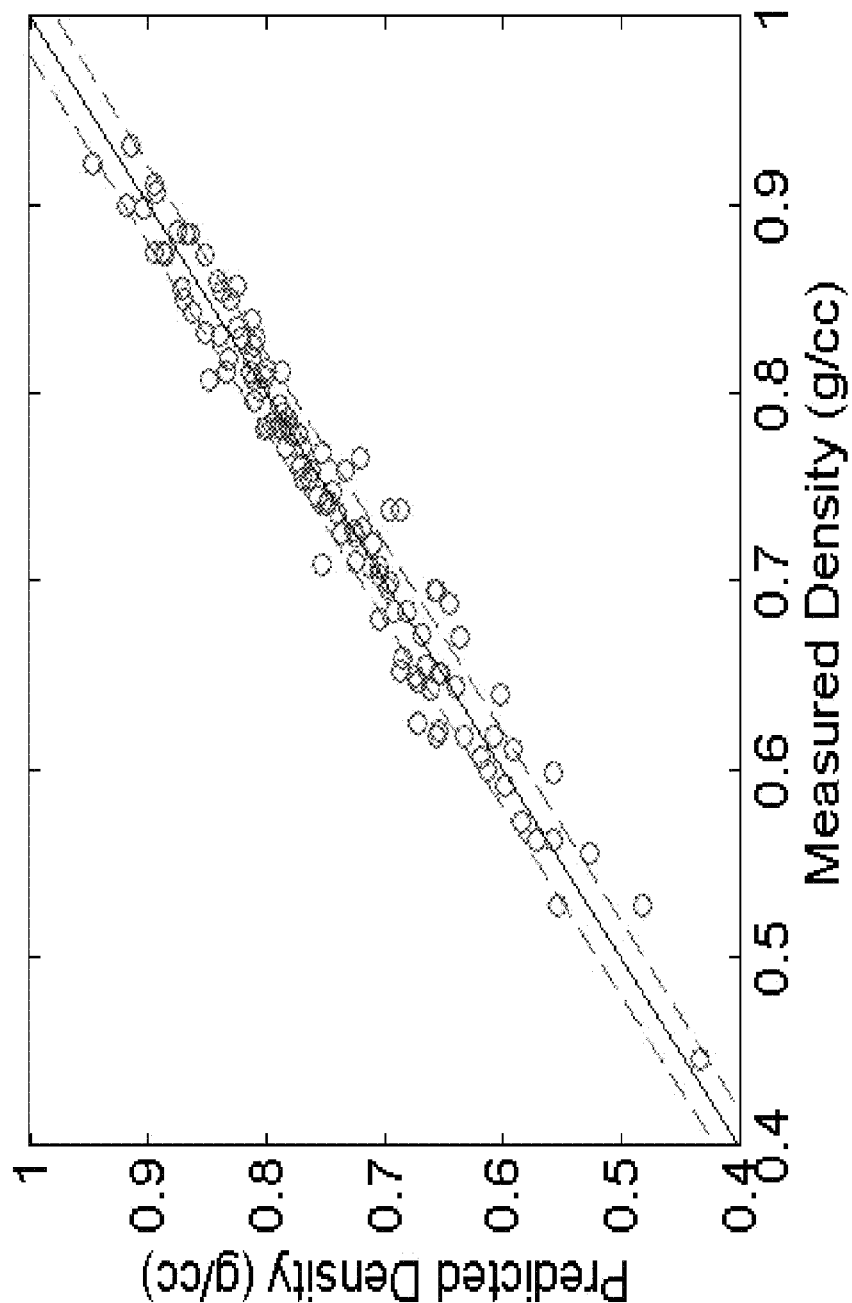
FIG. 10 is a graph that compares density values predicted using a model-independent mapping function technique with measured density values, in accordance with an aspect of the present disclosure.

The mapping function methodology described above can be similarly applied for quantitative prediction of live crude oil density from NMR measurements obtained using the NMR measurement system described above. Similar to Equation (6), the density of live crude oils may be expressed as a linear combination of normalized RBFs, such as Gaussian RBFs. The input vector $\vec{A}_T$ of such Gaussian functions may consist of normalized $T_1$, $T_2$ and D distributions, and normalized temperature (T) and pressure (P). FIG. 10 provides a graph showing the comparison of the live oil densities predicted using the above-mentioned leave-one-out method with the values measured in the laboratory. The solid line on the graph in FIG. 10 represents the best-fit line, and the dashed lines on either side of the solid line represent a deviation of ±0.020 g/cc. For the density predictions, Oil 3 was again excluded from the database for the construction of the mapping function for similar reasons (e.g., Oil 3 exhibited NMR relaxation time distributions more greatly affected by the presence of paramagnetic ions). For the density analysis, the optimal a, as determined from trial and error, was found to be about 1.0. The density predictions are obtained within an average absolute accuracy of approximately ±0.019 g/cc over the entire range. Thus, the results from this study show that the density of live crude oils at reservoir conditions can also be accurately predicted from NMR measurements obtained using the presently disclosed NMR measurement system.

Compressibility

Isothermal coefficient of compressibility is another important fluid property that is particularly useful for the solution of transient fluid flow problems, design of high pressure surface equipment, predicting acoustic wave velocities in crude oils, and in material balance calculations. The direct measurement of compressibility in the laboratory using, for example, PVT analysis is both expensive and time consuming. As noted above, compressibility was measured using for this experiment using a CCE instrument. Empirical models have been developed to predict compressibility of live crude oils from other fluid properties such as bubble point, density, etc. However, these models suffer from several fundamental limitations, i.e., they are too simple to be accurate, lack generality, and contain empirical parameters that can vary over a wide range.

Figure 11:
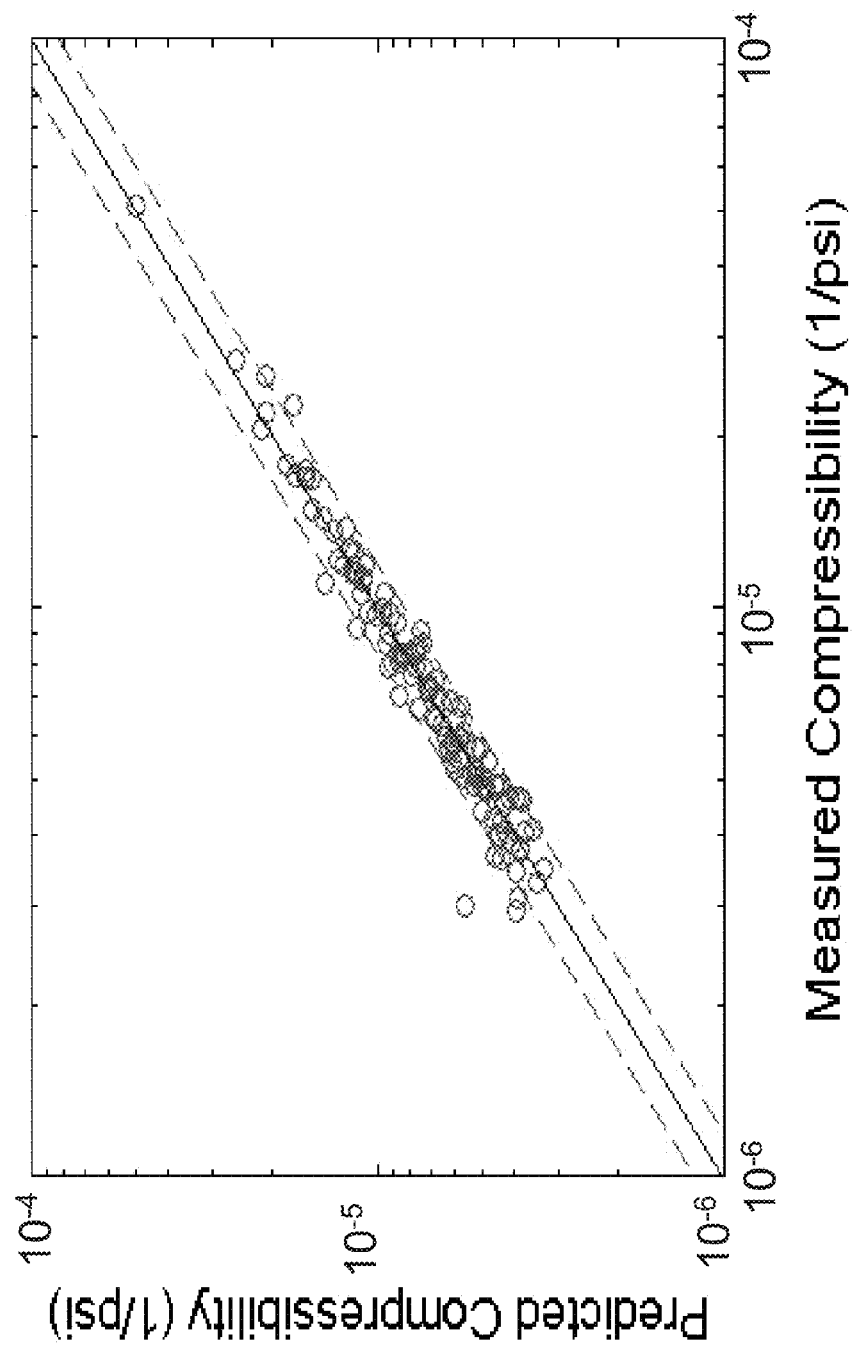
FIG. 11 is a graph that compares compressibility values predicted using a model-independent mapping function technique with measured compressibility values, in accordance with an aspect of the present disclosure.

To predict compressibility of live crude oils from NMR distributions measured using the NMR measurement system, a model-independent mapping function was constructed. The input vector for the mapping function consisted of normalized $T_1$, $T_2$ and D distributions, and normalized temperature (T) and pressure (P). FIG. 11 provides a graph showing the comparison of the compressibilities of the live oil samples predicted using the leave-one-out method with the compressibility values measured in the laboratory. The solid line on the graph of FIG. 11 represents the best-fit line, and the dashed lines on either side of the best-fit line represent a 20% deviation. Here, it was found that the predicted compressibility were within an average accuracy of approximately 8.4% over the entire range. For this particular experiment, the optimal a was found to be 2.0. Additionally, for the compressibility analysis, it was found that the addition of measurements made on Oil 3 in the database did not deteriorate the accuracy of predictions (as was the case for viscosity and density).

Formation Volume Factor

The formation volume factor of live crude oils is a measure of the shrinkage or reduction in the volume of the oil as it is produced. Accurate prediction of formation volume factor is a particularly useful parameter for the calculation of oil reserves and oil in place under stock tank conditions. Generally, the calculation of formation volume factor can be expressed as follows:

$$B_o = \frac{\text{Vol. of oil} + \text{gas @ reservoir press. and temp.}}{\text{Volume of stock tank oil}}. \quad (9)$$

Figure 12:
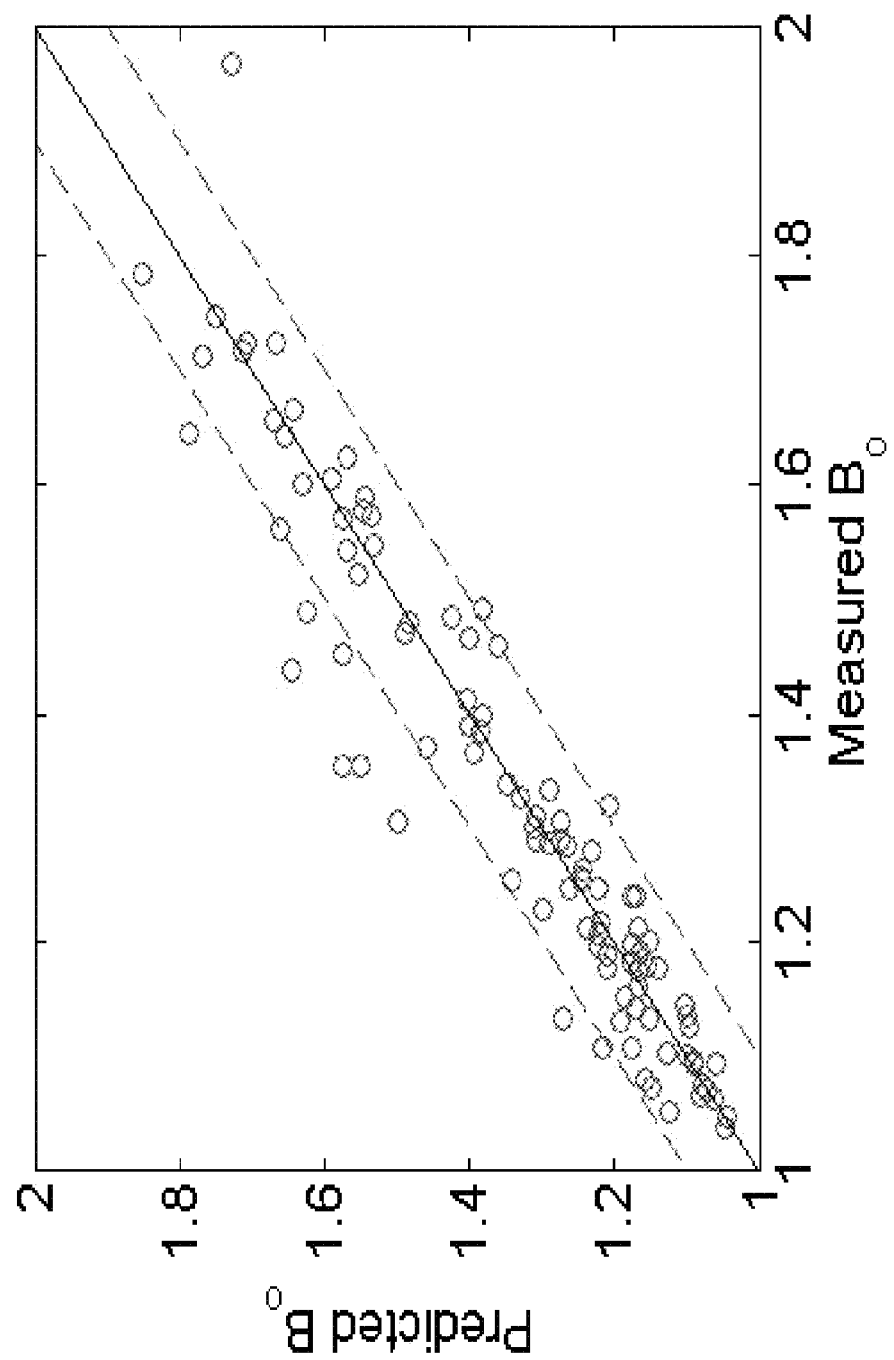
FIG. 12 is a graph that compares formation volume factor values predicted using a model-independent mapping function technique with formation value factors calculated based on measured gas-oil ratio, density, and specific gravity values, in accordance with an aspect of the present disclosure.

Previously, empirical equations have been proposed to predict formation volume factor based on compressibility and bubble point. However, these equations are approximate and require the knowledge of other fluid properties, i.e., compressibility and bubble point data. For the present experiment, the database did not include the measurements of formation volume factor for the suite of live crude oils. However, the values of the formation volume factor can be calculated from density and GOR of the live crude oils using the material balance calculation shown below:

$$B_o = \frac{62.4\,\gamma_o + 0.0136 \cdot GOR \cdot \gamma_g}{\rho_o}, \quad (10)$$

where $B_o$ is the formation volume factor, $\rho_o$ is the density of the oil in lb/ft$^3$, and $\gamma_o$ and $\gamma_g$ are the stock tank oil and gas specific gravities, respectively. The values of formation volume factor were computed at multiple temperatures and pressures using the measured values of live oil density, GOR, and specific gravities. A model-independent mapping function was constructed to relate the calculated $B_o$ to normalized $T_1$, $T_2$ and D distributions, and normalized temperature (T) and pressure (P). Referring to FIG. 12, a graph is provided showing the comparison of the predicted values of $B_o$ (using the leave-one-out method and the values calculated from Equation (10)). In FIG. 12, the solid line represents the best-fit line, and the dashed lines on either side of the best-fine line represent a deviation of 10%. Here, it was found that the predicted values of $B_o$ were within an average accuracy of 3.7% over the entire range.

Gas-Oil Ratio

Gas-oil ratio (GOR) is yet another important fluid property for a number or reasons, such as for material selection of well completions, design of surface facilities, and optimization or improvement of production techniques. It is understood that GOR is not a pressure and temperature dependent property. Hence, the measurements made on a live crude oil at multiple temperatures and pressures generally map to a single GOR value in the output space. As a result, the effective size of the database for prediction of GOR corresponds to the number of live crude oils in the database (e.g., 18 live oil samples in the present experiment).

Figure 13:
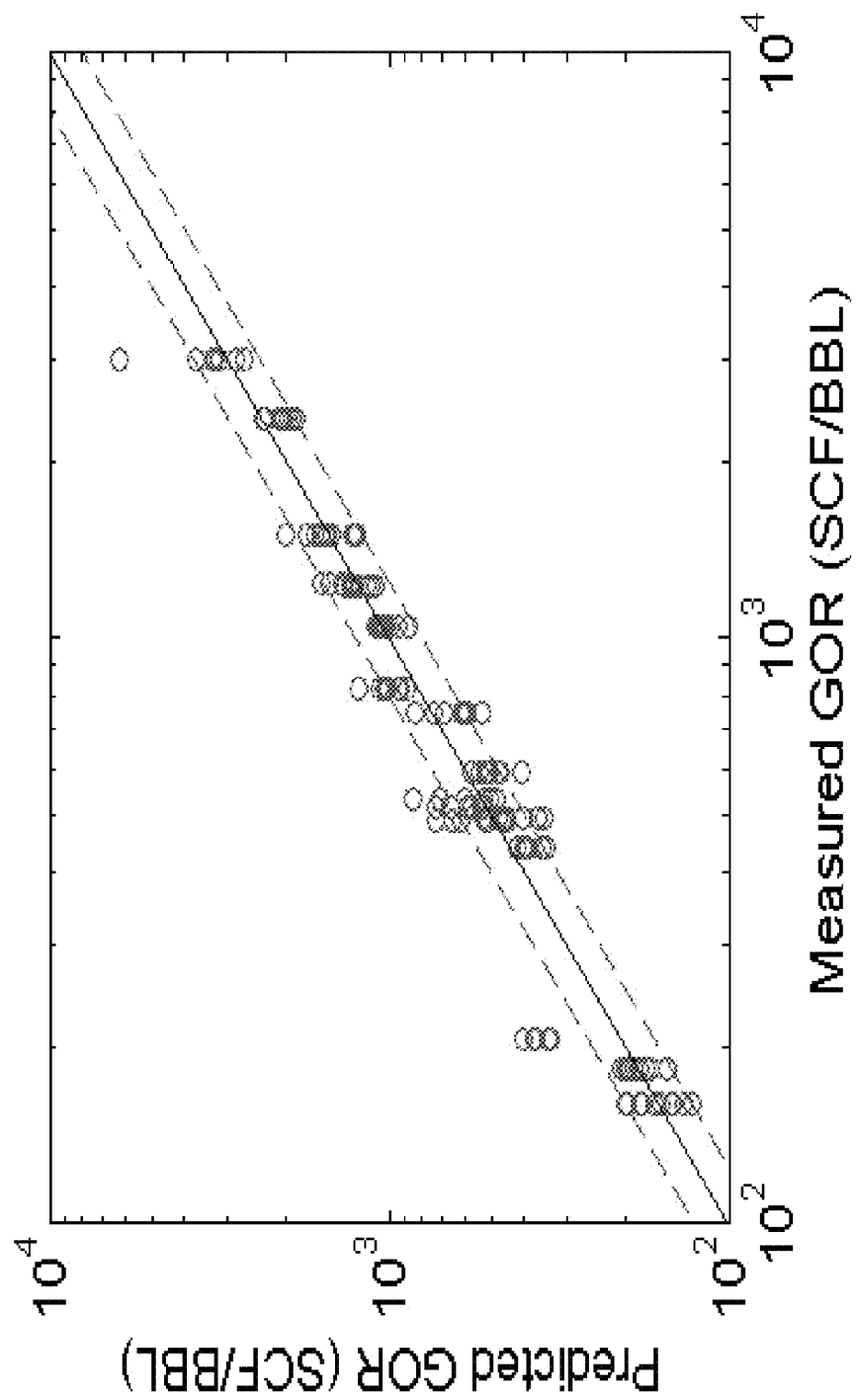
FIG. 13 is a graph that compares gas-oil ratios predicted using a model-independent mapping function technique with measured gas-oil ratios, in accordance with an aspect of the present disclosure.

Using the model-independent mapping function methodology, GOR was predicted using, for the input vector, normalized $T_1$, $T_2$, and D distributions, and normalized temperature (T) and pressure (P) as inputs. FIG. 13 shows a graph that compares the predicted GOR values (using the leave-one-out method) with the GOR values measured in the laboratory. The solid line in FIG. 13 represents the best-fit line, and the dashed lines on either side of the best-fit line represent a deviation of 20%. The optimal a was found to be about 3.0 in this case. Further, it was found that GOR was predicted to within an average accuracy of 17.2% over the entire range using the model-independent matching function technique. It is also expected that the accuracy of the predictions will improve given a larger sample suite of live oils in the database, i.e., a database with 30 oil samples.

Molecular Composition

As can be appreciated, the NMR relaxation time and diffusion distributions of live crude oils contain information on the molecular composition of crude oils. For example, the smaller molecules in a crude oil mixture typically have larger diffusion coefficients and longer relaxation times, and vice versa. However, the relationship between molecular composition and NMR distributions is a very complex function of the multitude of inter- and intra-molecular interactions between the different types of molecules present in the crude oil. Previous attempts at using simple idealized model to describe such complex interactions have been found to lack sufficient accuracy.

In this experiment, the molecular composition of live crude oils was predicted from the model-independent mapping function methodology using normalized $T_1$, $T_2$, and D distributions, and normalized temperature (T) and pressure (P) as inputs. Like GOR, molecular composition is not a temperature and pressure dependent property and, therefore, the effective size of the database is the number of live crude oils in the database (e.g., 18 live oil samples in the present experiment).

Figure 14A:
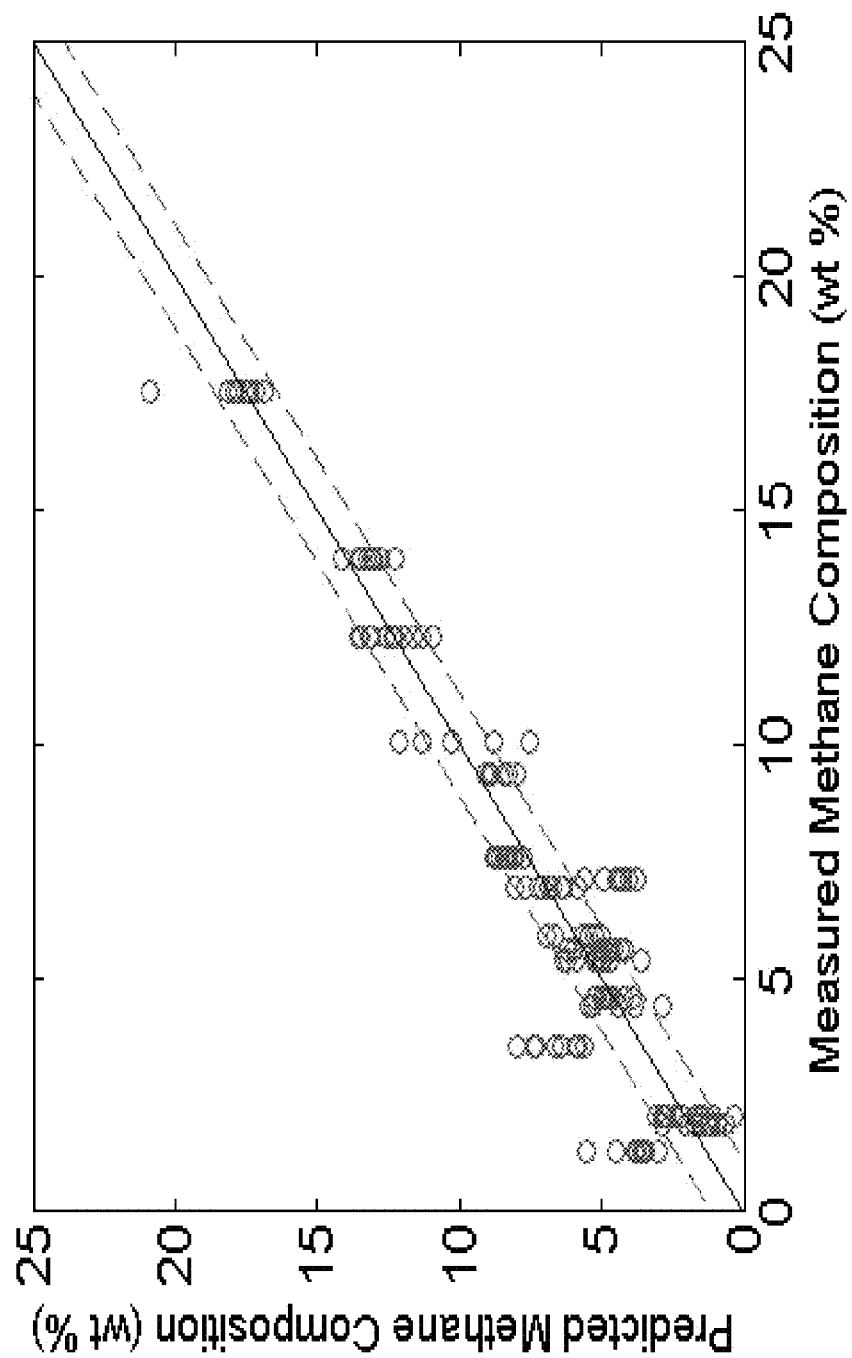
FIG. 14A is a graph that compares methane composition predicted using a model-independent mapping function technique with measured methane composition, in accordance with an aspect of the present disclosure.
Figure 14B:
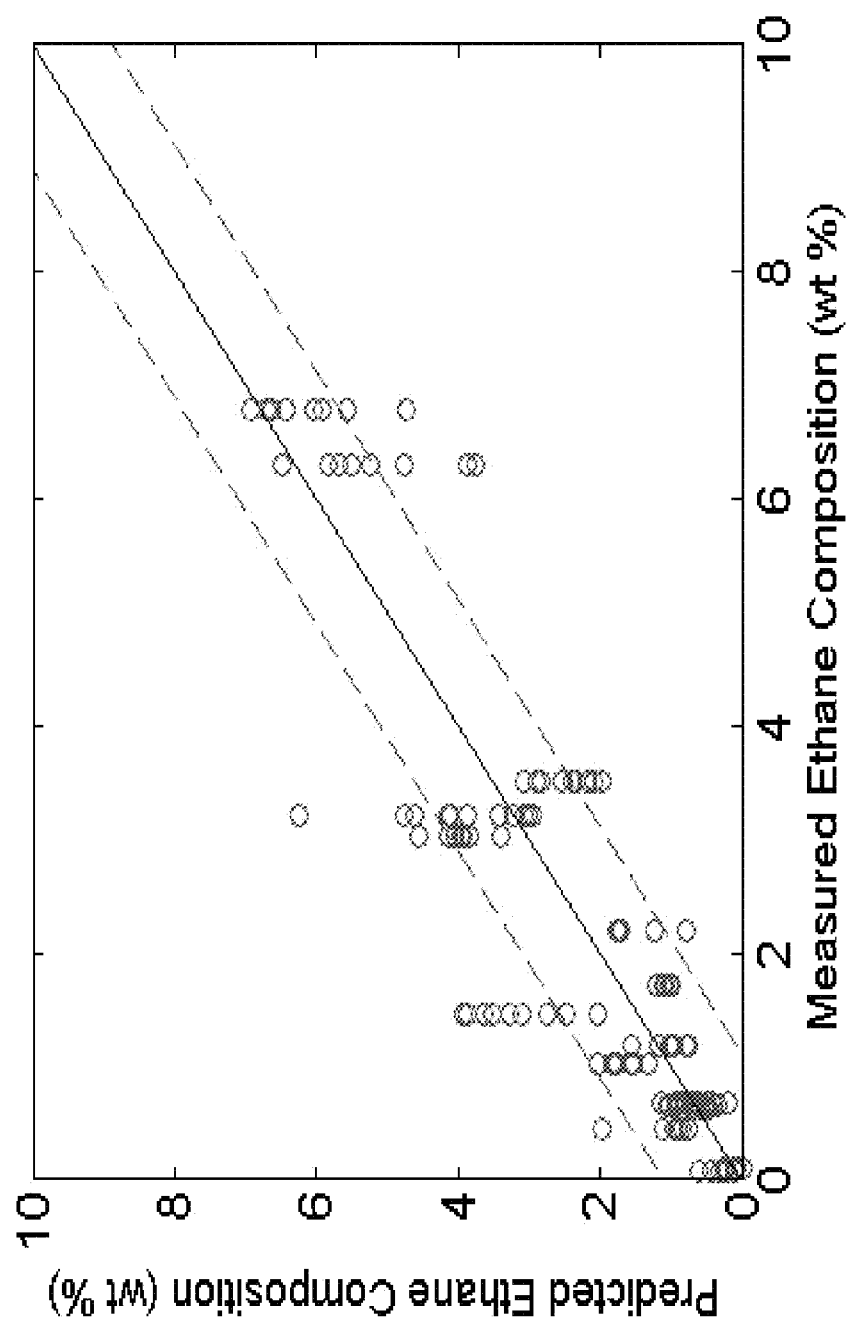
FIG. 14B is a graph that compares ethane composition predicted using a model-independent mapping function technique with measured ethane composition, in accordance with an aspect of the present disclosure.
Figure 14C:
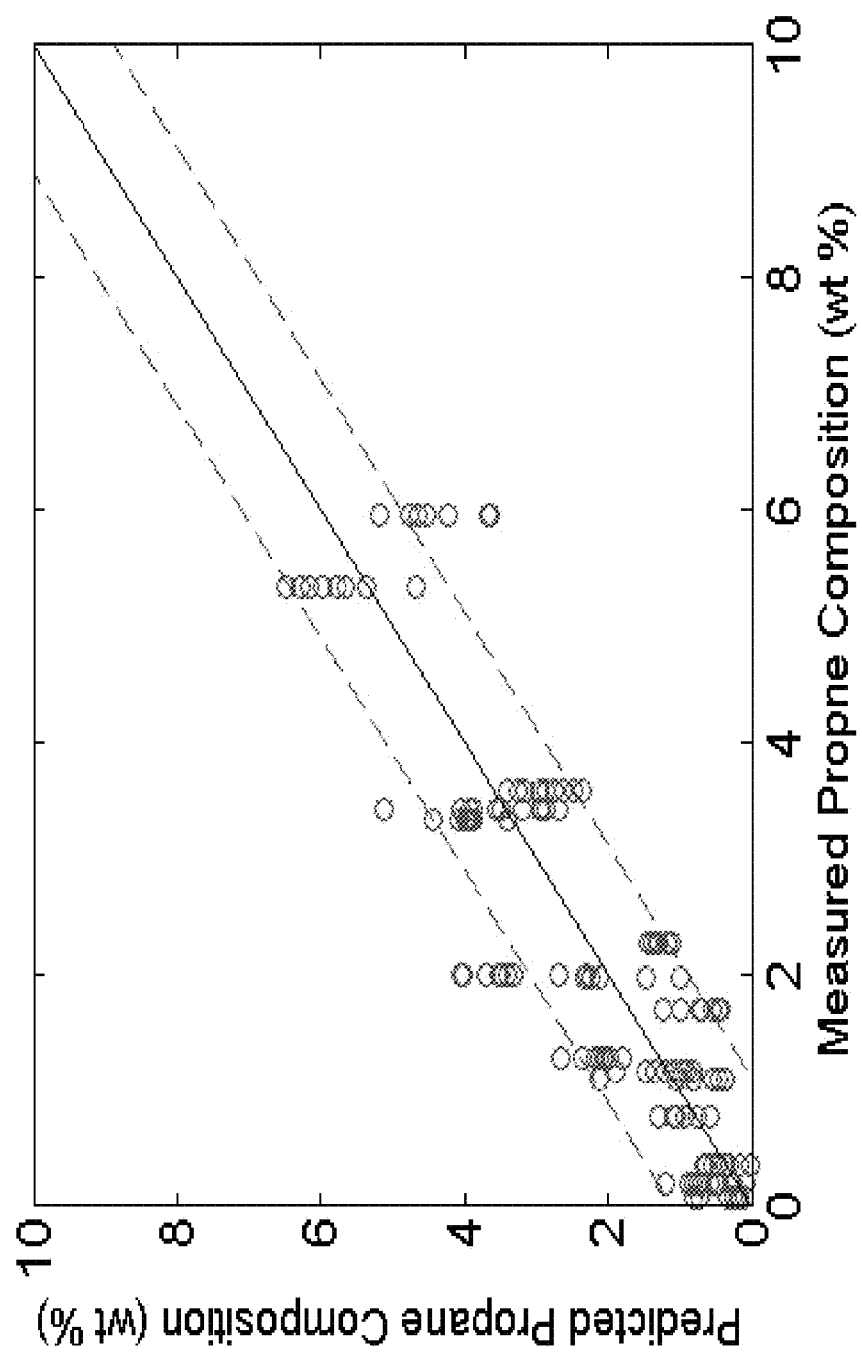
FIG. 14C is a graph that compares propane composition predicted using a model-independent mapping function technique with measured propane composition, in accordance with an aspect of the present disclosure.

FIGS. 14A, 14B, and 14C are graphs that show the methane (C1), ethane (C2), and propane (C3) compositions, respectively, as predicted from the model-independent mapping function methodology compared with those measured using gas chromatography. The notation C1, C2, etc., refers to the number of carbon atoms in a particular hydrocarbon component (e.g., C1 refers to methane ($CH_4$), C2 refers to ethane ($C_2H_6$), and so forth). For methane (FIG. 14A), the widths were kept fixed (e.g., $s_i$=4.0) while the widths for the other components (ethane (FIG. 14B) and propane (FIG. 14C)) were determined using Equation (8). It can be seen in FIGS. 14A-14C that the spread along the y-axis for each x-value corresponds to the predicted C1, C2, and C3 measurements at different temperatures and pressures. The solid line in each of FIGS. 14A-14C represents the best-fit line, and the dashed lines on either side of the best-fit line represent a deviation of 1 wt %. Here, it was found that the average absolute accuracies for the prediction of C1 (methane), C2 (ethane), and C3 (propane) were within 1.0, 0.62, and 0.63 wt %, respectively. Further, it was found that the additional hydrocarbon components C4-C29 and C30 and above (C30+) could be predicted within an average absolute accuracy of 0.54 (for C4-C29) and 3.0 wt % (for C30+), respectively. The scatter in the predictions arises due to the relatively small effective size of the database used in the present experiment.

Figure 15:
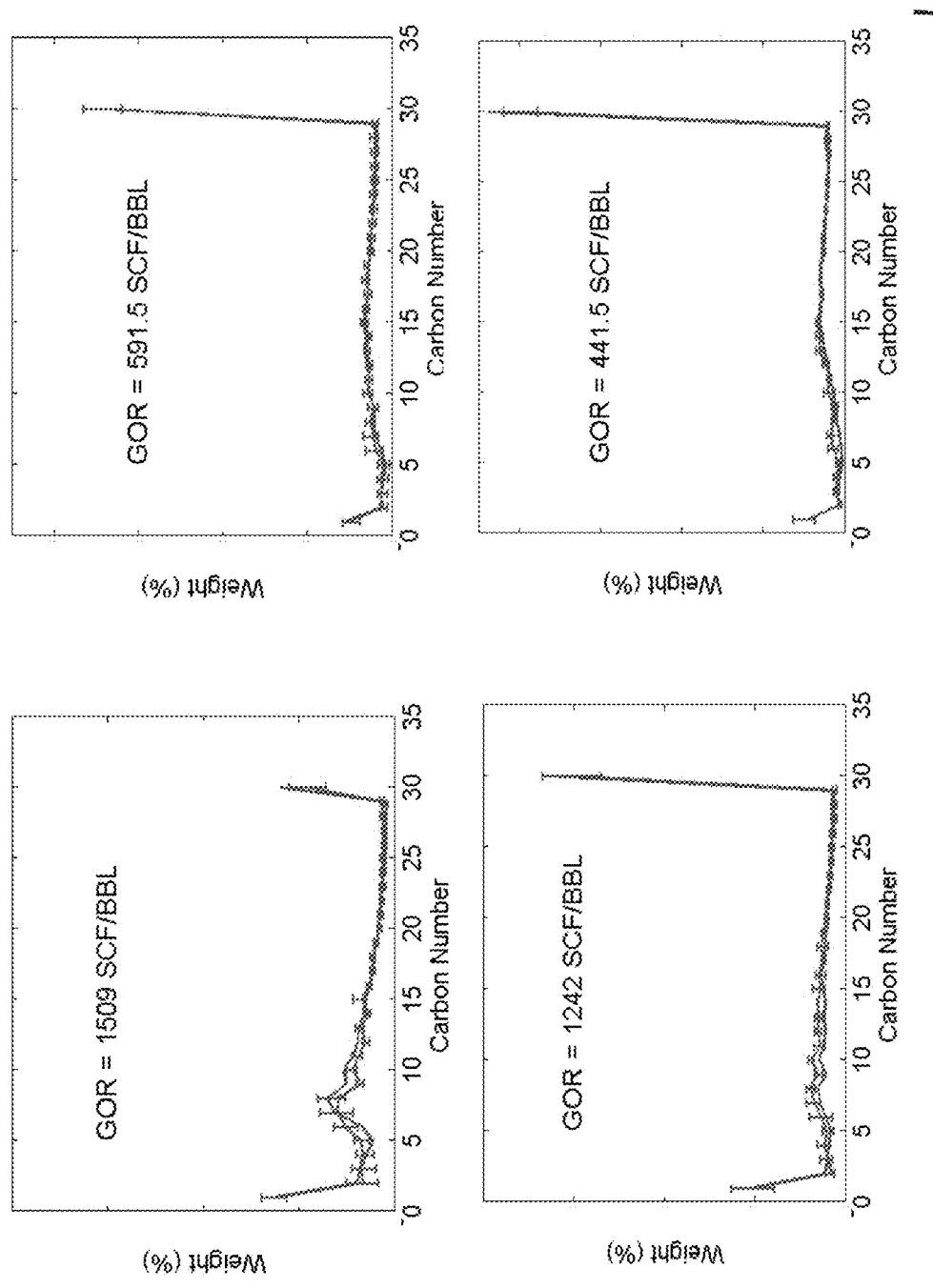
FIG. 15 shows graphically the comparison of the predicted molecular compositions of four live crude oil samples to measured molecular compositions for the same four live crude oil samples, in accordance with an aspect of the present disclosure.

FIG. 15 shows the molecular compositions predicted using the RBF model-independent mapping function technique for four live crude oils in the database with normalized $T_2$, and D distributions, and normalized temperature (T) and pressure (P) as inputs. The molecular compositions shown in FIG. 15 were obtained by averaging the predictions at multiple temperatures and pressures. The horizontal bars above and below the predicted value for each hydrocarbon component correspond to the maximum and minimum predicted values. The vertical lines, therefore, represent the spread in the predictions at multiple temperatures and pressures. For comparison, the molecular composition measured by gas chromatography on the same four live oils is also shown. It can be seen that there is generally good quantitative agreement between the predicted and measured molecular composition.

SARA Fraction

Figure 16:
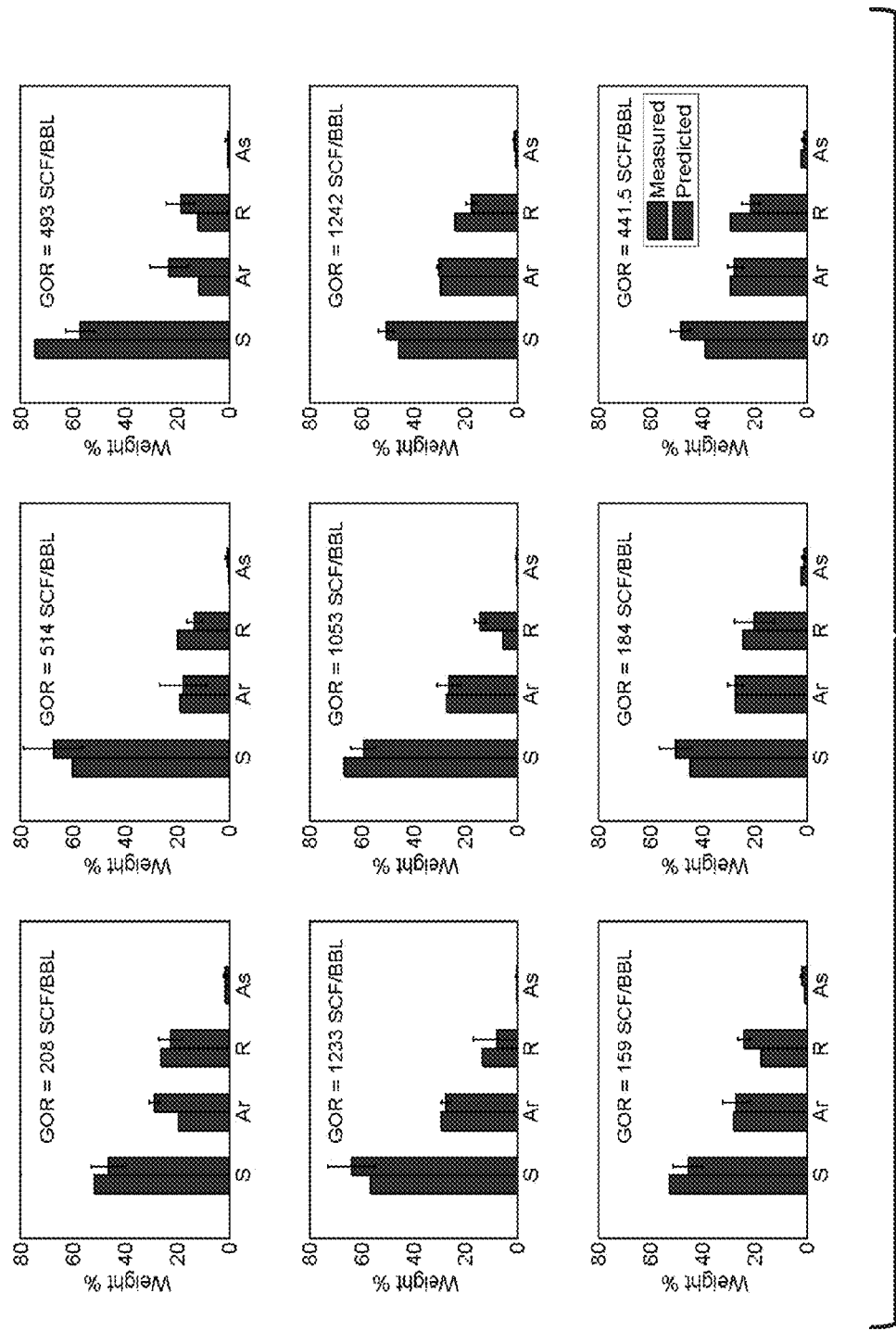
FIG. 16 shows graphically the comparison of the predicted SARA fractions of nine live crude oil samples to measured SARA fractions for the same nine live crude oil samples, in accordance with an aspect of the present disclosure.

The saturates, aromatics, resins, and asphaltene (SARA) fraction characterizes crude oils in four fractions of varying polarizability. FIG. 16 shows the comparison of SARA fractions predicted using the model-independent mapping function method for nine live crude oil samples with the SARA fractions measured in the laboratory. As noted above, the SARA fraction lab measurements were performed on dead oil versions of the live oils. Each graph in FIG. 16 corresponds to a respective one of the nine samples. The vertical bars in each graph of FIG. 16 correspond to the range of values predicted for each component (saturates, aromatics, resins, and asphaltenes) at different temperature and pressure conditions, wherein for each component, the right-side vertical bar denotes the predicted value and the left-side vertical bar denotes the measured value. As an example, the SARA fraction predictions made in this experiment used an input vector $\vec{A}_T$ that included normalized amplitudes of $T_1$, $T_2$ and D distributions, and normalized temperature (T) and pressure (P). The widths were determined such that a in Equation (8) was equal to about 0.5. Using these parameters, it was found that the SARA fractions are predicted within an average absolute accuracy of 7.0, 3.6, 6.4 and 0.48 wt %, respectively. Additionally, it was found that the addition of the D distribution in the input vector did not improve the accuracy of the asphaltene predictions. This conclusion is consistent with the above-stated observation (documented in the above-referenced Hurlimann 2009 publication) that D distributions of oils are not affected by the presence of asphaltenes.

4.2 Integration of NMR and Optical Density Measurements

The model-independent RBF mapping function methodology described herein allows for the relatively straightforward integration of different types of measurements for prediction of fluid properties. For instance, this integration can be performed by including the optical and NMR measurements in the input vector. The integration does not add additional complexity to the computations. For this particular experiment, the near-infrared (NIR) optical density (OD) spectra of the live oils in the database for wavelengths in the range from 1500 nm to 2000 nm were used in the integration. The optical absorption in this wavelength range is dominated by molecular vibrations in hydrocarbons. Fluid properties were predicted from the RBF mapping function in Equation (2), where the input vector, $\vec{A}_T$, consisted of normalized amplitudes of $T_1$, $T_2$, and D distributions, OD, and normalized temperature (T) and pressure (P), as shown below:

$$\vec{A}_T = \vec{A}_T(A(T_1), A(T_2), A(D), OD, T, P). \quad (11)$$

As was stated above with reference to FIGS. 8A and 8B, the shape of the absorption spectra for live oils is generally independent of temperature and pressure. However, the amplitudes of the spectra change with temperature and pressure. Therefore, for temperature and pressure independent fluid properties, such as molecular composition, GOR etc., the absorption spectra were normalized with the largest amplitude in order to remove the temperature and pressure dependence. For fluid properties that were dependent on temperature and pressure, such as compressibility, density, viscosity, etc., the absorption spectra were not normalized, thus preserving the temperature and pressure dependency.

Here, it was found that the integration of optical density measurements with NMR measurements in the input vector of the RBF mapping function did not yield significant improvement in the predictions of viscosity, density, compressibility, formation volume factor, and GOR. A small improvement in the predictions of C1 (methane) weight fraction was observed with the integration of the NMR distributions and the OD spectrum. Specifically, in the present experiment, the predicted weight fraction of C1 when using NMR measurements and optical measurements improved to an average accuracy of 0.88 wt % from a 1.0 wt % average accuracy when using NMR measurements alone. However, no significant improvement was observed in the predictions of molecular fractions for C2 and higher by integration of NMR and optical density measurements. Accordingly, these results clearly show that NMR distributions contain much more information on molecular composition and other fluid properties than do infrared OD measurements. Further, in other embodiments, instead or in addition to optical measurements, the NMR measurements may be combined with density, resistivity, and/or dielectric, or other types of measurements.

Section 6: Conclusions

The present disclosure has provided a description of a system and methodology for predicting fluid properties based on NMR measurements taken on live oils using a model-independent RBF mapping function technique. To summarize, the various topics discussed in the present disclosure include the following: (1) an extensive database of NMR measurements, optical measurements, and fluid property measurements acquired at multiple temperatures and pressures (e.g., up to 175 C and 25 kpsi); (2) a high performance NMR measurement system used to perform the high pressure and temperature measurements; and (3) the prediction of fluid properties such as viscosity, density, compressibility, molecular composition, gas-oil ratio, and SARA fractions from NMR measurements and the accuracies of those predictions when compared with the corresponding measured fluid properties.

The present disclosure has also demonstrated that NMR measurements can be used to accurately predict molecular composition (C1-C29, C30+), SARA fractions, GOR, viscosity, compressibility, density, and formation volume factor. It was demonstrated that accurate fluid properties can be quantitatively predicted from a database of NMR and fluid properties measurements using a model-independent mapping function method derived from radial basis functions. Further, it was shown that integrating optical density measurements with NMR measurements resulted in essentially no improvement in the predicted compositions. The accuracies of the fluid properties predicted from NMR measurements for the live crude oils in the database used for this experiment are shown below in Table 1.

TABLE 1

ACCURACIES OF FLUID PROPERTIES PREDICTED FROM NMR MEASUREMENTS
Summary of NMR Fluid Properties Predictions

| Fluid Property | Database Ranges of Fluid Properties | Accuracy of NMR Prediction |
|---|---|---|
| C1 | 1.3-17.6 wt % | 1 wt % |
| C2 | 0.08-6.8 wt % | 0.62 wt % |
| C3 | 0.07-5.9 wt % | 0.63 wt % |
| C4-C29 | 1.6-3.2 wt % | 0.54 wt % |
| C30+ | 7.7-47.3 wt % | 3 wt % |
| Saturates | 38.7-74.6 wt % | 7.0 wt % |
| Aromatics | 11.7-30.5 wt % | 3.6 wt % |
| Resins | 5.3-29.4 wt % | 6.4 wt % |
| Asphaltenes | 0.1-2.2 wt % | 0.48 wt % |
| GOR | 150-3000 SCF/BBL | 19.4% |

TABLE 1-continued

ACCURACIES OF FLUID PROPERTIES
PREDICTED FROM NMR MEASUREMENTS
Summary of NMR Fluid Properties Predictions

| Fluid Property | Database Ranges of Fluid Properties | Accuracy of NMR Prediction |
|---|---|---|
| Viscosity | 0.1-80 cp | 10.6% |
| Compressibility | (3-40) × $10^{-6}$ $psi^{-1}$ | 8.4% |
| Density | 0.43-0.93 g/cc | 0.019 g/cc |
| Formation Volume Factor | 1.05-1.95 | 3.7% |

While the specific embodiments described above have been shown by way of example, it will be appreciated that many modifications and other embodiments will come to the mind of one skilled in the art having the benefit of the teachings presented in the foregoing description and the associated drawings. Accordingly, it is understood that various modifications and embodiments are intended to be included within the scope of the appended claims.

What is claimed is:

1. A nuclear magnetic resonance (NMR) measurement system comprising:
a sensor assembly comprising a sample holder having a body defining an interior cavity for receiving a fluid sample, a frame member disposed in the interior cavity of the sample holder, an antenna coil disposed in the interior cavity about the frame member, an inlet that allows the fluid sample to enter the interior cavity, an outlet that allows for the fluid sample to be flushed from the interior cavity, and a magnet assembly having a central bore in which the sample holder is disposed; and
pulse sequencer circuitry that supplies signals to the antenna coil;
wherein, when the interior cavity of the sample holder is filled with the fluid sample, the antenna coil and the frame member are at least partially submerged in the fluid sample, and the antenna coil is configured to obtain NMR measurements of the fluid sample in response to the signals wherein the NMR measurements comprise at least one of a longitudinal relaxation time distribution ($T_1$), a transverse relaxation time distribution ($T_2$), a diffusion distribution (D), or a hydrogen index (HI) a computing system having non-transitory memory that stores a database comprising laboratory measurements for a plurality of reservoir fluid samples, wherein the computing system is configured to receive the obtained NMR measurements, provide the obtained NMR measurements as inputs to a model-independent mapping function based on radial basis functions, predicting a fluid property based on an output of the model-independent mapping function;
wherein the model-independent mapping function is determined using a database comprising NMR and fluid property measurements obtained on a plurality of reservoir fluids at a plurality of temperatures and pressures.

2. A method for predicting a fluid property of a reservoir fluid comprising:
placing a nuclear magnetic resonance system into a downhole environment;
obtaining a sample of the reservoir fluid and transferring the sample into a sample holder of a sensor assembly of the nuclear magnetic resonance (NMR) measurement system, such that the sample fills the sample holder, the sample holder having a radio frequency antenna disposed therein that is submerged in the sample when filled, and wherein the sample holder is disposed within a magnet assembly and adjacent to a pair of pulse field gradient coils;
obtaining NMR measurements on the sample at a given temperature and pressure;
using the NMR measurements, temperature, and pressure as inputs to a model-independent mapping function based on radial basis functions; and
predicting the fluid property based on an output of the model-independent mapping function;
wherein the model-independent mapping function is determined using a database comprising NMR and fluid property measurements obtained on a plurality of reservoir fluids at a plurality of temperatures and pressures.

3. The method of claim 2, wherein the fluid property comprises at least one of viscosity, density, molecular composition, SARA fractions, formation volume factor, gas-oil ratio, or compressibility.

4. The method of claim 2, wherein the radial basis functions are Gaussian functions.

5. The method of claim 2, wherein obtaining the NMR measurements includes supplying a bipolar pulse field gradient sequence to the pair of pulse field gradient coils.

6. The method of claim 2, wherein obtaining the NMR measurements at the given temperature and pressure comprises obtaining at least one of a longitudinal relaxation time distribution ($T_1$), a transverse relaxation time distribution ($T_2$), a diffusion distribution (D), or hydrogen index (HI).

7. The method of claim 2, wherein the model-independent mapping function is expressed using the following equation:

$$\vec{F}(\vec{x}) = \frac{\sum_{i=1}^{N} \vec{c}_i \exp\left(-\frac{\|\vec{x}-\vec{x}_i\|^2}{2s_i^2}\right)}{\sum_{i=1}^{N} \exp\left(-\frac{\|\vec{x}-\vec{x}_i\|^2}{2s_i^2}\right)}$$

wherein $\vec{F}(\vec{x})$ represents the fluid property, N represents the number of measurements in the database, $\vec{x}_i$ represents a vector containing database inputs for the i-th measurement, $\vec{x}$ represents a vector containing measurements made on the sample, and $s_i$ represents the width of the radial basis function corresponding to the i-th measurement.

8. The method of claim 7, wherein the mapping function is a scalar function when the fluid property being predicted is a single component property, and wherein the mapping function is a vector function when the fluid property being predicted is a multi-component fluid property.

9. A downhole tool disposable in a wellbore penetrating a formation, the downhole tool comprising:
a probe for obtaining a fluid sample from the formation;
a nuclear magnetic resonance (NMR) sensor assembly comprising a sample holder having a body that defines an interior cavity for receiving the fluid sample, an antenna coil disposed in the interior cavity, an inlet that allows the fluid sample to enter the interior cavity, an outlet that allows for the fluid sample to be flushed from the interior cavity, first and second pulse field gradient coils arranged adjacent to the sample holder, and a magnet assembly in which the sample holder and the first and second pulse field gradient coils are disposed, wherein the antenna coil is arranged such that it is least partially submerged and in direct contact with the fluid sample as the fluid sample fills the interior cavity; and pulse sequencer circuitry that supplies measurement signals to the antenna coil and the pulse field gradient coils;

wherein, when the interior cavity of the sample holder is filled with the fluid sample, the antenna coil is configured to obtain at least one of a longitudinal relaxation time distribution ($T_1$) measurement, a transverse relaxation time distribution ($T_2$) measurement, or a hydrogen index (HI) on the fluid sample and the first and second pulse field gradient coils are configured to obtain a diffusion distribution (D) measurement on the fluid sample in response to the supplied signals and further comprising processing logic that receives the measurements obtained by the antenna coil and/or the pulse field gradient coils, inputs the received measurements to a model-independent mapping function based on radial basis functions, and predicts the fluid property of interest based on the output of the model-independent mapping function, wherein the model-independent mapping function is determined using a database comprising NMR and fluid property measurements obtained on a plurality of reservoir fluids at a plurality of temperatures and pressures.

10. The downhole tool of claim 9, wherein the fluid property of interest comprises at least one of viscosity, density, molecular composition, SARA fractions, formation volume factor, gas-oil ratio, or compressibility.

* * * * *